United States Patent
Otto et al.

(10) Patent No.: US 7,842,092 B2
(45) Date of Patent: Nov. 30, 2010

(54) PROSTHETIC DEVICE AND SYSTEM AND METHOD FOR IMPLANTING PROSTHETIC DEVICE

(75) Inventors: Jason K. Otto, Plantation, FL (US); Binyamin Hajaj, Plantation, FL (US); Rony Abovitz, Hollywood, FL (US); Amit Mistry, Plantation, FL (US); Scott Nortman, Sunrise, FL (US); Steven B. Brown, Coral Springs, FL (US)

(73) Assignee: Mako Surgical Corp., Ft. Lauderdale, FL (US)

( * ) Notice: Subject to any disclaimer, the term of this patent is extended or adjusted under 35 U.S.C. 154(b) by 14 days.

(21) Appl. No.: 11/617,449

(22) Filed: Dec. 28, 2006

(65) Prior Publication Data

US 2007/0219639 A1 Sep. 20, 2007

Related U.S. Application Data

(60) Provisional application No. 60/782,356, filed on Mar. 14, 2006.

(51) Int. Cl.
*A61F 2/30* (2006.01)
(52) U.S. Cl. .................. 623/18.11; 623/20.14; 623/908; 623/914
(58) Field of Classification Search .................. 623/194, 623/20.15, 20.19, 20.21, 20.3, 914, 908; 703/11
See application file for complete search history.

(56) References Cited

U.S. PATENT DOCUMENTS

| | | | |
|---|---|---|---|
| 5,042,504 A | 8/1991 | Huberti | |
| 5,533,519 A | 7/1996 | Radke et al. | |
| 5,935,171 A | 8/1999 | Schneider et al. | |
| 6,033,415 A | 3/2000 | Mittelstadt et al. | |
| 6,170,488 B1 | 1/2001 | Spillman, Jr. et al. | |
| 6,171,252 B1 | 1/2001 | Roberts | |
| 6,205,411 B1 * | 3/2001 | DiGioia et al. | 703/11 |
| 6,206,835 B1 | 3/2001 | Spillman, Jr. | |
| 6,322,567 B1 | 11/2001 | Mittelstadt et al. | |

(Continued)

FOREIGN PATENT DOCUMENTS

EP 1 208 820 A2 5/2002

(Continued)

OTHER PUBLICATIONS

"virtual." Merriam-Webster Online Dictionary. 2009. Merriam-Webster Online. Sep. 4, 2009 <http://www.merriam-webstercom/dictionary/virtual>.*

(Continued)

*Primary Examiner*—David H Willse
*Assistant Examiner*—Megan Wolf
(74) *Attorney, Agent, or Firm*—Foley and Lardner LLP

(57) ABSTRACT

A prosthetic device includes one or more components configured to be disposed in a joint. The component includes at least one feature configured to provide information about the component. The information can be used to determine or create the relationship between the component and the joint and/or other components. This relationship may be used to evaluate and/or modify the expected performance of the prosthetic device and assist in determining the optimal relationship between one or more components and a patient's anatomy.

2 Claims, 17 Drawing Sheets

F

U.S. PATENT DOCUMENTS

| | | | |
|---|---|---|---|
| 6,447,448 | B1 | 9/2002 | Ishikawa et al. |
| 6,583,630 | B2 | 6/2003 | Mendes et al. |
| 6,610,096 | B2 | 8/2003 | MacDonald |
| 6,621,278 | B2 | 9/2003 | Ariav |
| 6,706,005 | B2 | 3/2004 | Roy et al. |
| 6,856,141 | B2 | 2/2005 | Ariav |
| 6,984,993 | B2 | 1/2006 | Ariav |
| 7,080,554 | B2 | 7/2006 | Ariav et al. |
| 7,097,662 | B2 | 8/2006 | Evans, III et al. |
| 7,190,273 | B2 | 3/2007 | Liao et al. |
| 7,195,645 | B2 | 3/2007 | Disilvestro et al. |
| 7,634,306 | B2 | 12/2009 | Sarin et al. |
| 2003/0069591 | A1* | 4/2003 | Carson et al. ............... 606/130 |
| 2004/0152970 | A1* | 8/2004 | Hunter et al. ............... 600/424 |
| 2005/0251065 | A1* | 11/2005 | Henning et al. ............. 600/587 |
| 2005/0267584 | A1* | 12/2005 | Burdulis et al. .......... 623/20.19 |
| 2006/0029795 | A1 | 2/2006 | Sawyer et al. |
| 2006/0030681 | A1 | 2/2006 | Sawyer et al. |
| 2006/0133827 | A1 | 6/2006 | Becouarn et al. |
| 2006/0142657 | A1 | 6/2006 | Quaid et al. |
| 2006/0224088 | A1 | 10/2006 | Roche |

FOREIGN PATENT DOCUMENTS

| | | |
|---|---|---|
| WO | WO 98/41152 A | 9/1998 |
| WO | WO 01/35872 A | 5/2001 |
| WO | WO 03/030738 A | 4/2003 |
| WO | WO 2005/039440 A | 5/2005 |

OTHER PUBLICATIONS

Morris et al., "e-knee: Evolution of the Electronic Knee Prosthesis: Telemetry Technology Development," *The Journal of Bone & Joint Surgery*, vol. 83-A, Supplement 2, Part 1, 2001.

Townsend et al., "Micro Datalogging Transceiver Networks for Dynamic Activity & Structural Performance Monitoring," Microstrain Presentation from www.microstrain.com. Date unknown but probably in the 2001 to 2003 timeframe. 1999-2007, according to www.microstrain.com.

* cited by examiner

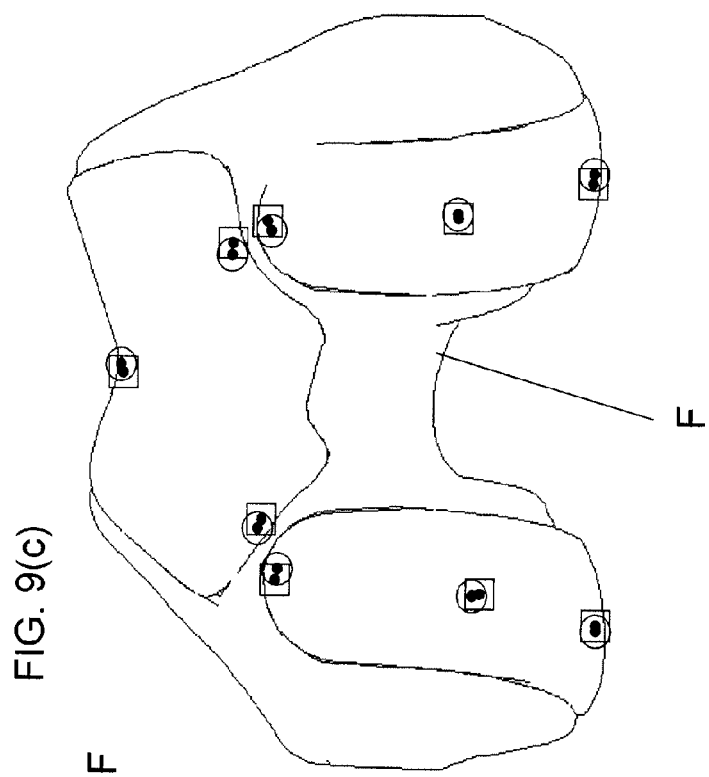
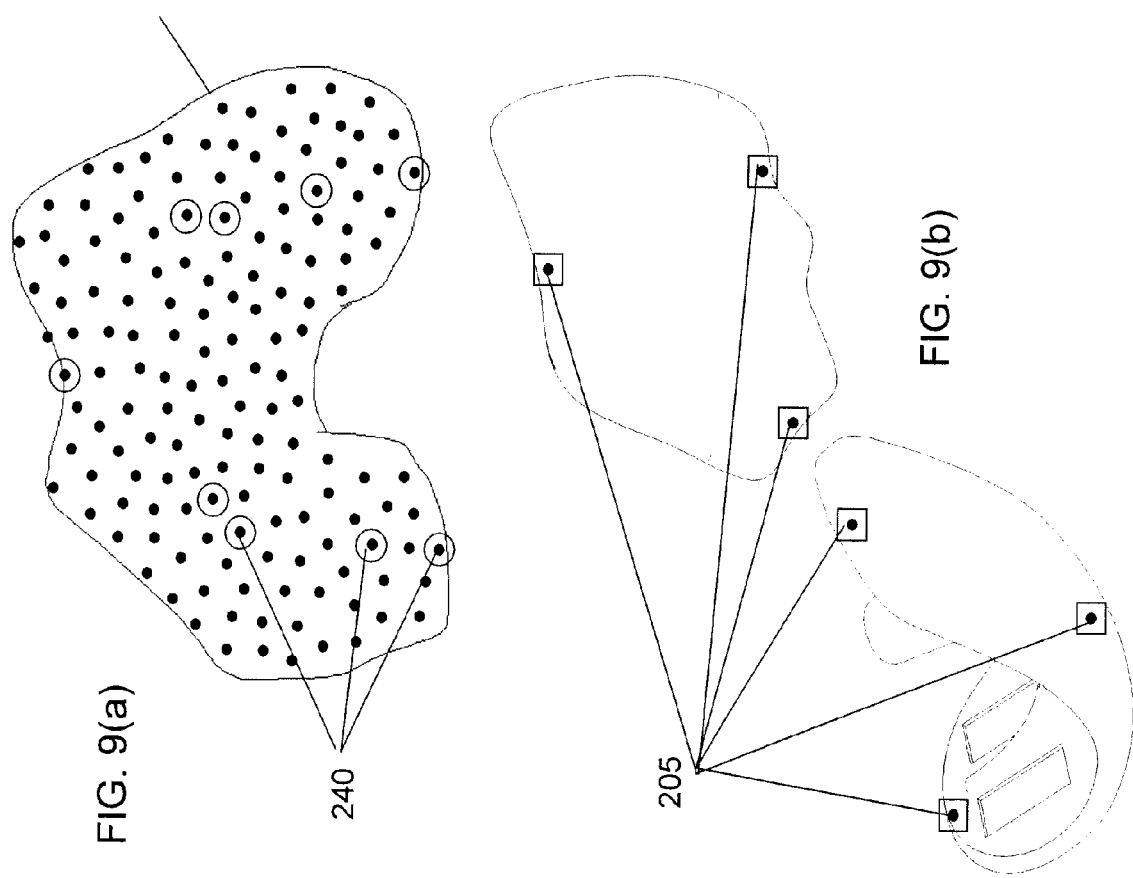

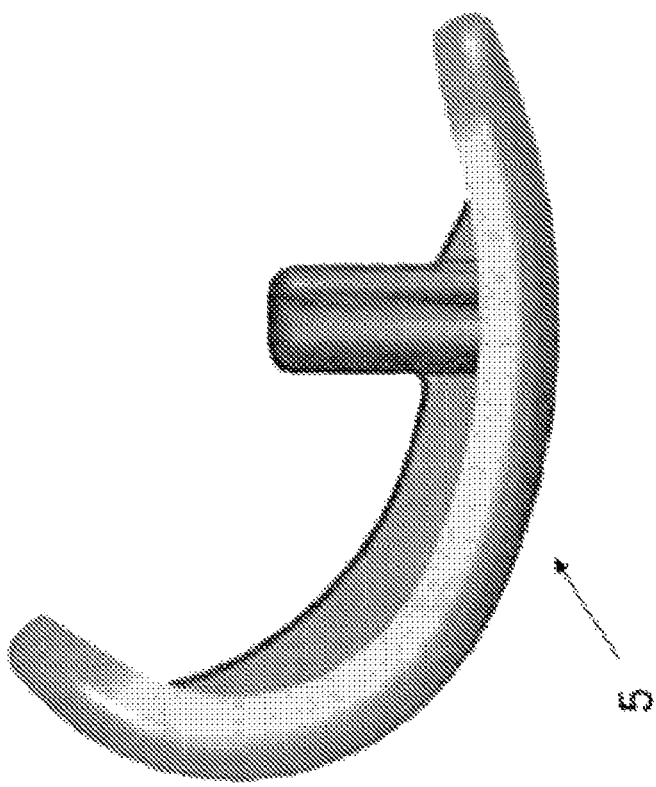
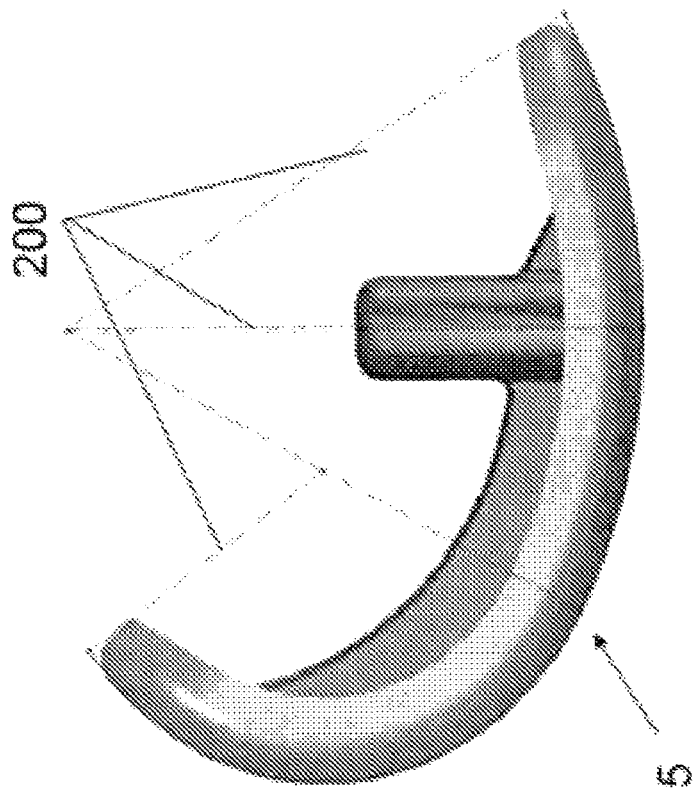

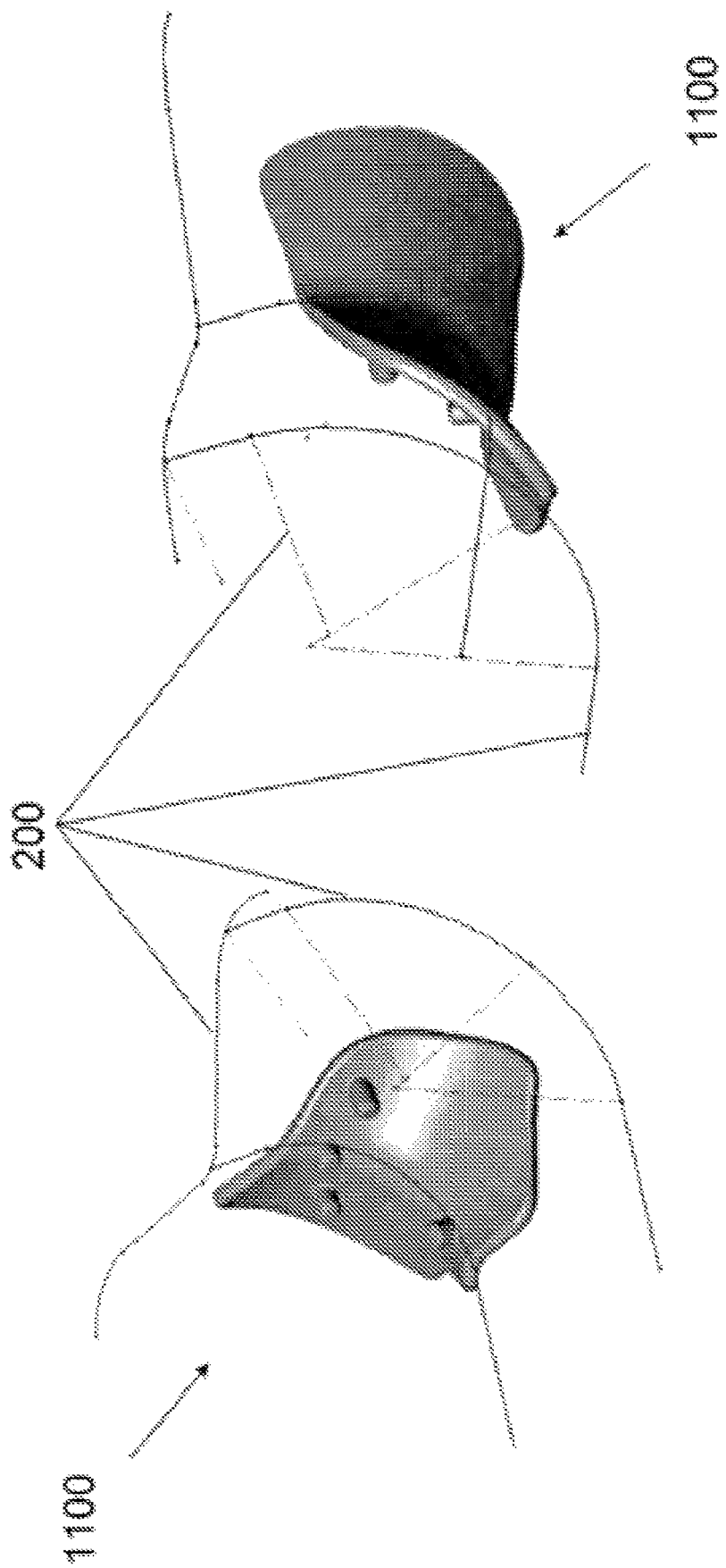

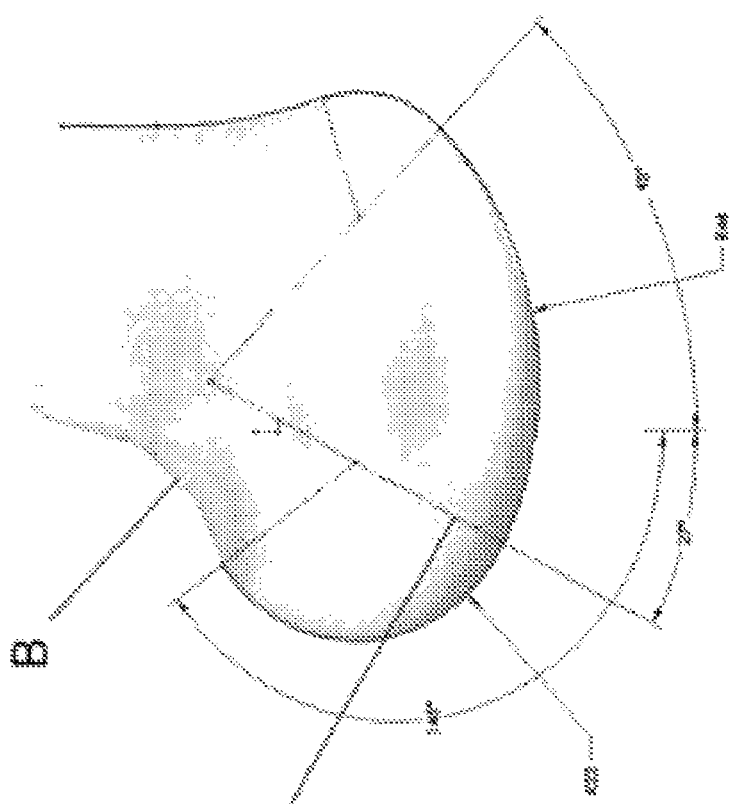
FIG. 12(a)
FIG. 12(b)

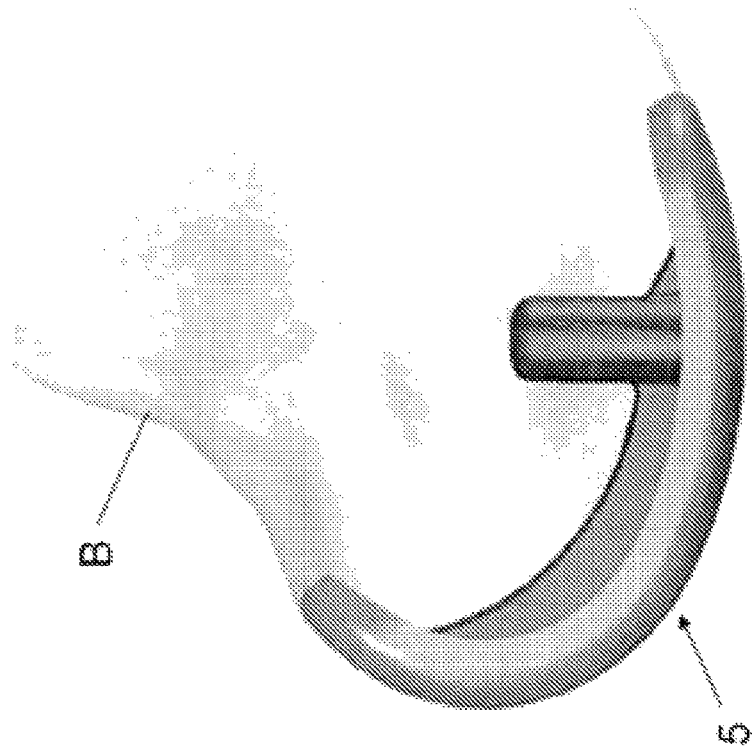
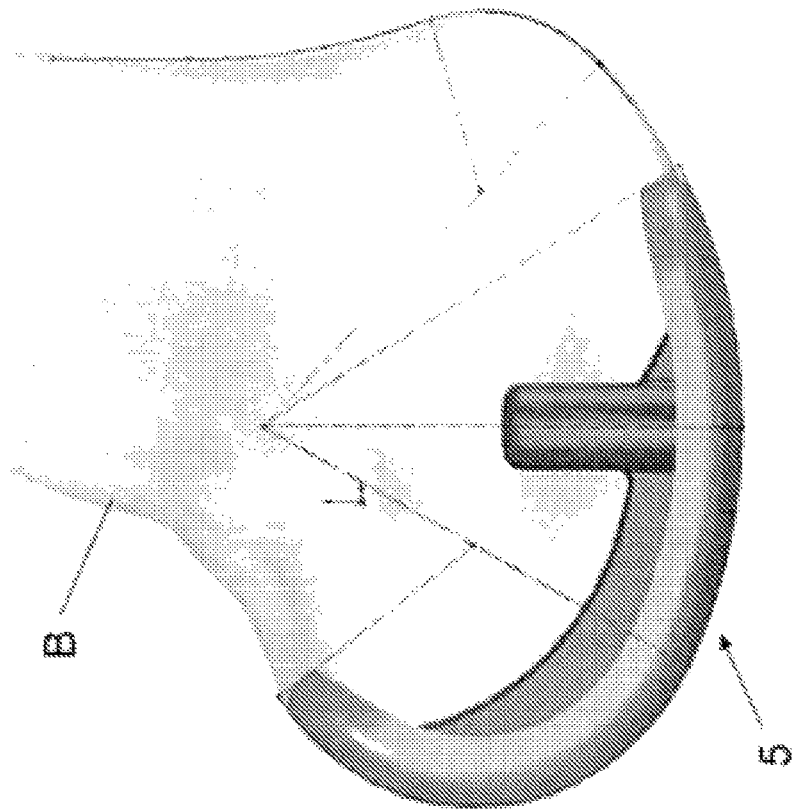

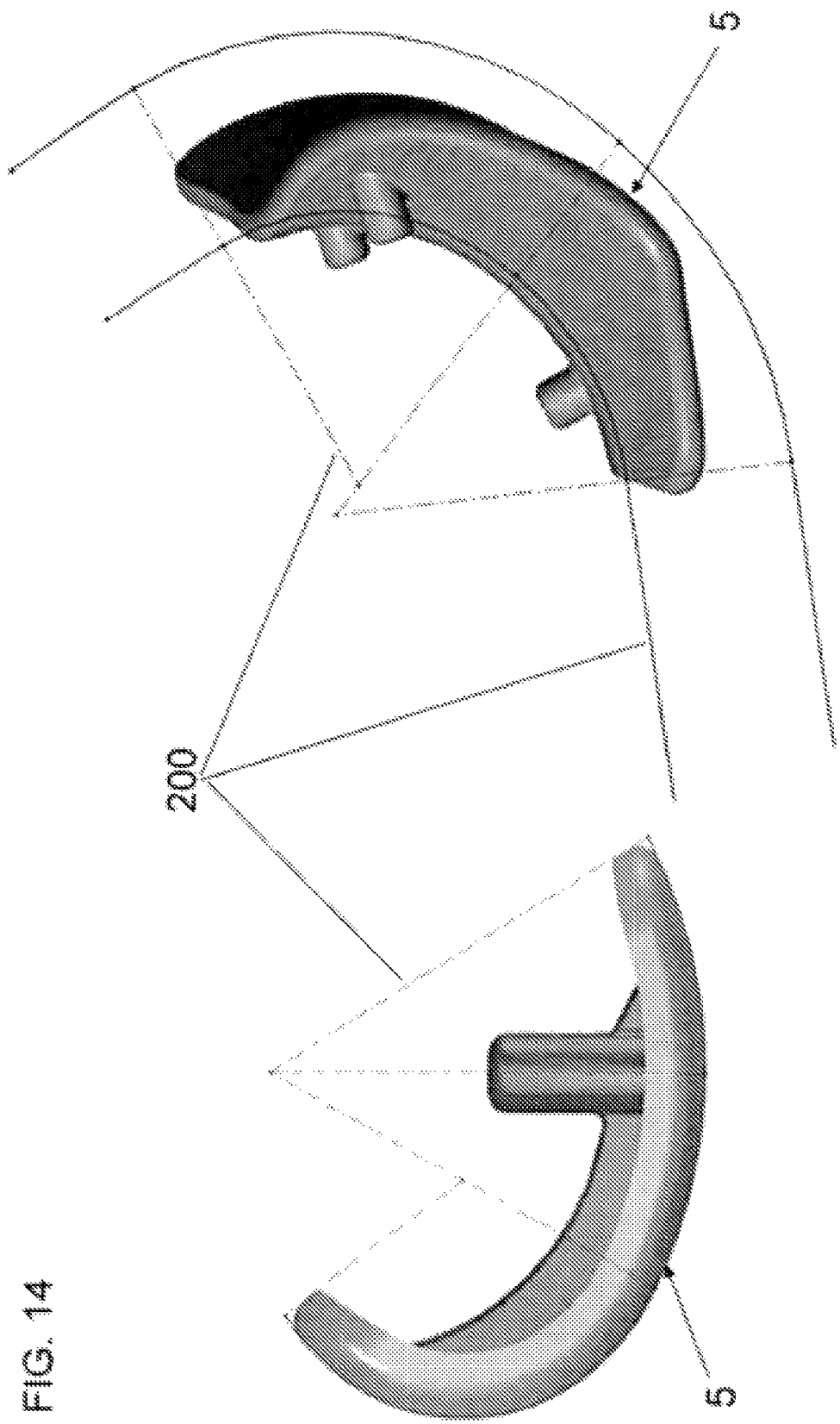

PROSTHETIC DEVICE AND SYSTEM AND METHOD FOR IMPLANTING PROSTHETIC DEVICE

BACKGROUND OF THE INVENTION

1. Field of the Invention

The invention relates to orthopedic joint replacement and, more particularly, to a prosthetic device for use in orthopedic joint replacement and a system and method for implanting the same.

2. Description of Related Art

As shown in FIG. 1, conventional total knee arthroplasty (TKA) systems typically include a femoral component 500 that is implanted on the distal end of the femur and replaces the bearing surfaces of the femur, a tibial component 502 that is implanted on the proximal end of the tibia and replaces the bearing surfaces of the tibia, and a patellar component (not shown) that replaces the undersurface of the patella. The tibial component 502 typically includes a tibial baseplate (or tray) 502a that is affixed to the bone and a tibial insert 502b that is disposed on the tibial baseplate 502a and forms the bearing surfaces of the tibial component 502. In operation, the bearing surfaces of the femoral component 500 articulate against the bearing surfaces of the tibial component 502 as the knee joint moves through a range of motion.

One disadvantage of conventional TKA systems is that they limit the ability to perform surgery through MIS incisions. For example, the femoral component 500 and the tibial component 502 are too large to fit through minimally invasive surgery (MIS) incisions, which are considerably smaller than incisions used in traditional surgical approaches. Another disadvantage is that the femoral component 500 and the tibial component 502 have fixed geometry and are available in a limited range of sizes. As a result, the surgeon may be unable to achieve an optimal fit for each patient and may be forced to remove healthy as well as diseased bone to accommodate the implant. Thus, conventional TKA systems lack the flexibility to enable the surgeon to select implant components that are customized to accommodate a patient's unique anatomy and/or disease state.

In an effort to overcome these disadvantages, modular knee prostheses comprising multiple components that are inserted separately and assembled within the surgical site have been developed. One example of a modular system is described in U.S. patent application Ser. No. 11/312,741, filed Dec. 30, 2005, which is hereby incorporated by reference herein in its entirety. Computer aided design can be used to create a variety of components, certain of which are intended to provide a more customized fit based on a patient's particular circumstances and characteristics (e.g., anatomy and/or disease state). Such modular systems offer increased flexibility to the surgeon and may result in an improved fit. Such systems present a challenge, however, as they generally require a high degree of insertion accuracy to properly place the components relative to one another. For example, whereas the femoral component 500 of a conventional TKA system comprises a solid part having a fixed geometry (as shown in FIG. 1), a modular system may be constructed of individual modular components that are each separately implanted in the joint. Thus, the geometry of a modular system is variable depending on the surgeon's placement of the separate modular components relative to one another. To ensure that a proper geometric relationship (e.g., distance, orientation, alignment, etc.) is established among all modular components, each modular component must be inserted (or positioned) in the joint with a high degree of accuracy. Achieving the requisite accuracy requires significant surgical skill as well as specialized instruments and technology. Because surgeons have different skill levels and experience, operative results among patients may not be sufficiently predictable and/or repeatable. As a result, modular implant performance and longevity may vary among patients.

Another disadvantage of both conventional and modular knee implants is that monitoring implant wear and relative position over time in a non-invasive manner is difficult. For example, although installed implants may be imaged using X-ray or other imaging technologies, such images do not provide sufficient clarity and/or detail to enable precise tracking of implant wear and relative position. As a result, surgeons are often unable to predict precisely when an implant will need to be replaced or to determine the condition of soft tissue in the joint in a non-invasive manner.

In view of the foregoing, a need exists for techniques and implants that enable improved insertion accuracy and relative placement of implant components and non-invasive monitoring of implant wear and relative position.

SUMMARY OF THE INVENTION

According to an aspect of the present invention, a prosthetic device is provided. The prosthetic device includes a component configured to be disposed in a joint. The component includes at least one feature configured to provide information about the component.

According to another aspect of the present invention, a collection of components for forming a prosthetic device is provided. The collection of components includes a first component configured to be disposed in a joint and a second component configured to be disposed in the joint. The first component includes a first feature configured to convey information about the first component, and the second component includes a second feature configured to convey information about the second component.

According to yet another aspect of the present invention, a surgical method is provided. The surgical method includes the steps of acquiring information about a first implant disposed in a joint; acquiring information about a second implant disposed in the joint; and determining a relationship between the first implant and the second implant based at least in part on the information acquired about the first implant and the information acquired about the second implant.

According to yet another aspect of the present invention, a surgical method is provided. The surgical method includes the steps of acquiring information about a first implant disposed in a joint and planning placement in the joint of a second implant based at least in part on the information acquired about the first implant and a desired relationship between the first implant and the second implant.

According to yet another aspect of the present invention, a system for implanting a prosthetic device is provided. The system includes a first component configured to be disposed in a joint and a second component configured to be disposed in the joint. The first component includes a first feature, and the second component includes a second feature. The system also includes a computer programmed to determine a relationship between the first component and the second component based at least in part on the first feature and the second feature.

According to still another aspect of the present invention, a system for implanting a prosthetic device is provided. The system includes a first component configured to be disposed in a joint having a first feature. In addition, the system includes a second component configured to be disposed in a joint including a second feature. The system also includes a computer programmed to create at least one relationship between the first component and the second component based at least in part on the first feature and the second feature. The computer is also programmed to evaluate the relationship based on at least one condition.

According to still another aspect of the present invention, a system for implanting a prosthetic device is provided. The system includes a plurality of components configured to be disposed in a joint. Each component includes at least one feature providing information. The system also includes a computer programmed to create at least one relationship between the plurality of components based at least in part on the feature of the plurality of components, and to evaluate the relationship based on at least one condition.

According to still another aspect of the present invention, a surgical method is provided. The surgical method includes the steps of acquiring a first feature of a first component configured to be disposed in a joint, acquiring a second feature of a second component configured to be disposed in the joint, determining a relationship between the first feature and the second feature; and evaluating the relationship based on at least one condition.

According to still another aspect of the present invention, a surgical method is provided. The surgical method includes the steps of acquiring a first feature of a first component of a joint, acquiring a second feature of a second component of the joint, relating the first feature to the second feature based on a relationship, and modifying the relationship based on a performance characteristic.

According to still another aspect of the present invention, a surgical method is provided. The surgical method includes the steps of acquiring a feature of a plurality of components configured to be disposed in a joint, creating a relationship between the features of the plurality of components, and evaluating the relationship based on at least one condition.

BRIEF DESCRIPTION OF THE DRAWINGS

The accompanying drawings, which are incorporated in and constitute a part of this specification, illustrate embodiments of the invention and together with the description serve to explain principles of the invention.

FIGS. 9(a)-9(c) are perspective views of an embodiment of a prosthetic device according to the present invention and a plan view of a femur of a patient.

FIGS. 10(a)-10(d) are perspective and plan views of an embodiment of a prosthetic device according to the present invention.

FIGS. 11(a)-11(b) are perspective views of an embodiment of a prosthetic device according to the present invention.

FIGS. 12(a)-12(c) are plan views of a bone of a patient.

FIGS. 13(a)-13(b) are plan views of an embodiment of a prosthetic device according to the present invention implanted into the bone of a patient.

FIG. 14 is a plan view of an embodiment of two prosthetic device components according to the present invention.

DETAILED DESCRIPTION OF PREFERRED EMBODIMENTS

Figure 1:
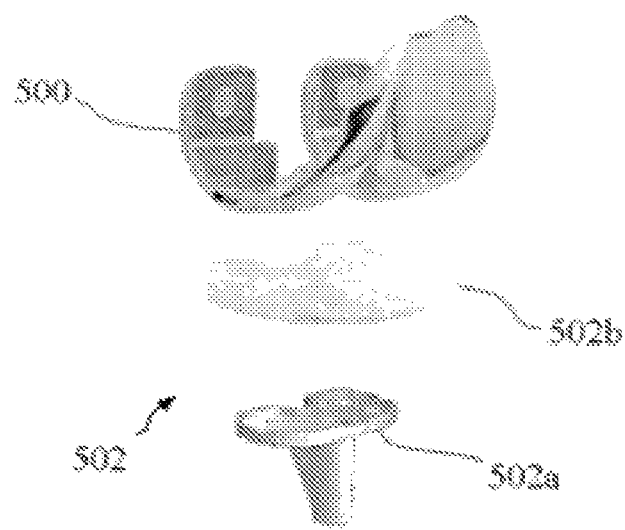
FIG. 1 is a perspective view of a conventional total knee arthroplasty system.

Presently preferred embodiments of the invention are illustrated in the drawings. An effort has been made to use the same or like reference numbers throughout the drawings to refer to the same or like parts.

Figure 2:
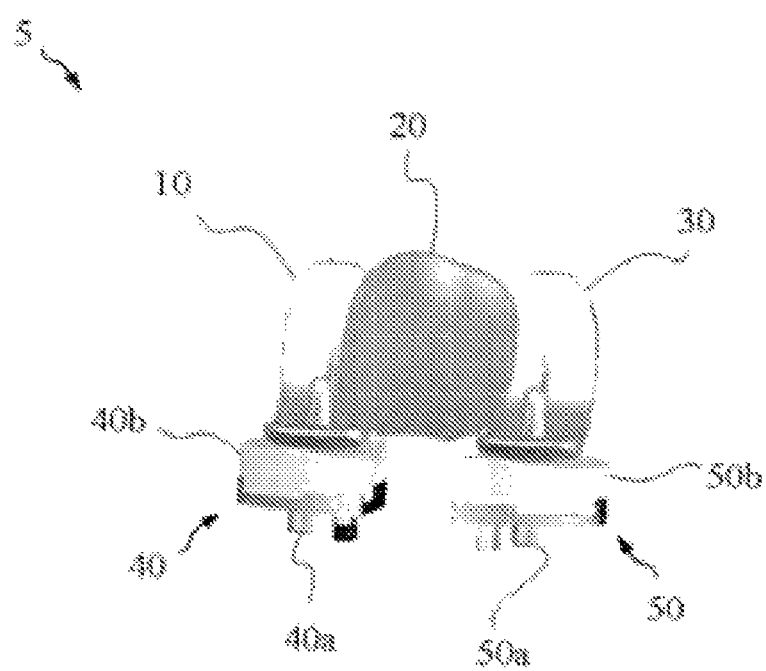
FIG. 2 is a perspective view of an embodiment of a prosthetic device according to the present invention.

FIG. 2 shows an embodiment of a prosthetic device 5 according to the present invention. In this embodiment, the prosthetic device 5 is a modular total knee implant. The prosthetic device 5, however, is not limited to knee implants. The prosthetic device 5 may be any orthopedic joint implant, such as, for example, a total knee implant; a unicondylar knee implant; a modular knee implant; implants for other joints including hip, shoulder, elbow, wrist, ankle, and spine; and/or any other orthopedic and/or musculoskeletal implant, including implants of conventional materials and more exotic implants, such as orthobiologics, drug delivery implants, and cell delivery implants. In the alternative the prosthetic device may be a trial of an implant. In one embodiment, the implant is a modular knee implant as described in U.S. patent application Ser. No. 11/312,741, filed Dec. 30, 2005, which is hereby incorporated by reference herein in its entirety.

The prosthetic device 5 of FIG. 2 includes a femoral portion and a tibial portion formed from a collection of modular components. The femoral portion includes a first component 10, a second component 20, and a third component 30. The tibial portion includes a fourth component 40 and a fifth component 50. Each component of the prosthetic device 5 preferably includes at least one feature configured to provide information about the component.

Figure 3:
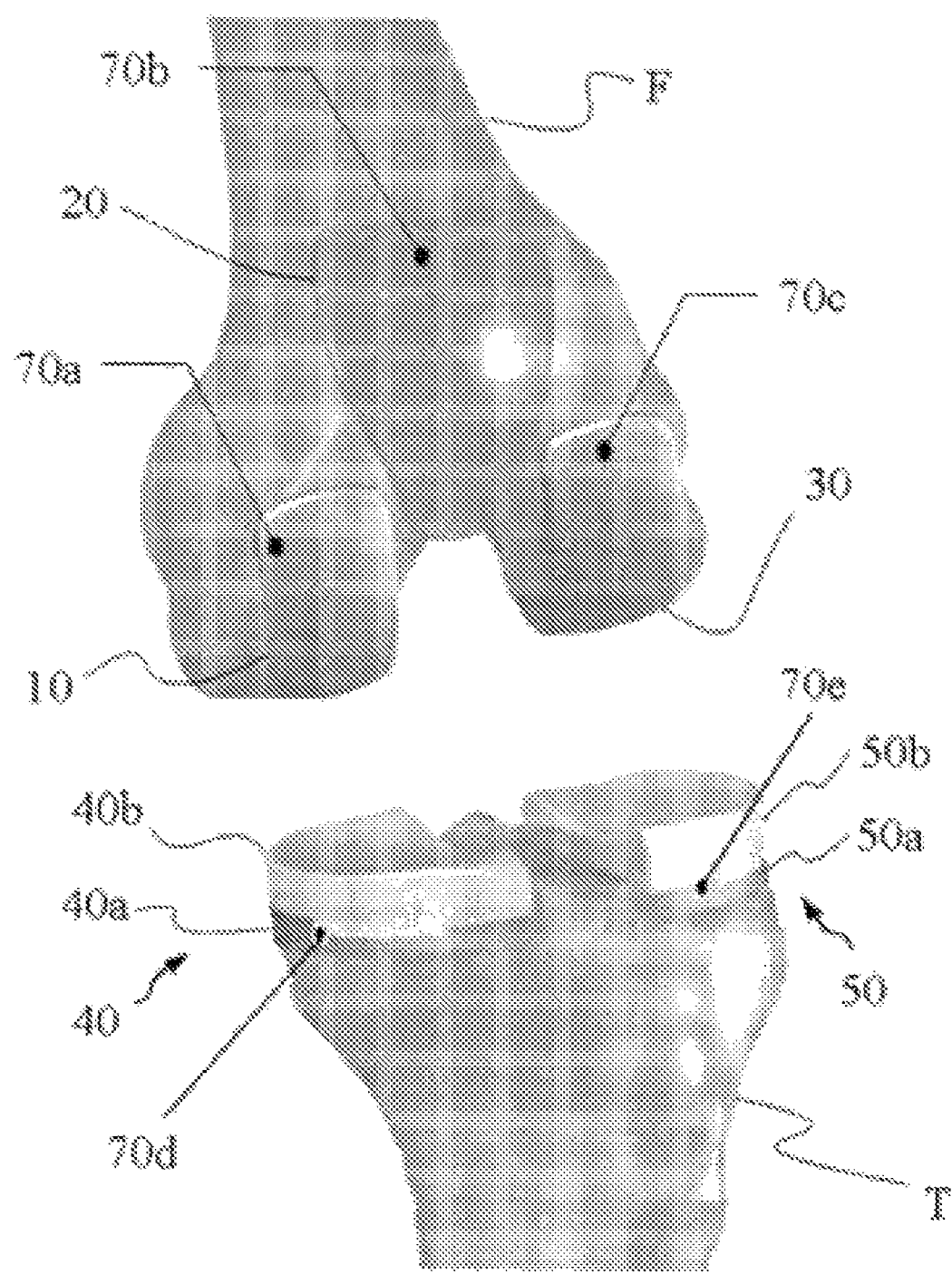
FIG. 3 is a perspective view of the prosthetic device of FIG. 2 implanted on a femur and a tibia of a patient.

As shown in FIG. 3, the first component 10 of the femoral portion of the prosthetic device 5 is a femoral component configured to be disposed on a medial or lateral condyle of a femur F of a knee joint. The third component 30 is configured to be disposed on the opposite condyle of the femur F and may be similar to or different from the first component 10. In this embodiment, the third component is substantially similar to the first component 10. The second component 20 is a patello-femoral (PF) component configured to be disposed between the first and third components 10 and 30 on the PF joint of the femur F.

The tibial portion of the prosthetic device 5 includes the fourth and fifth components 40 and 50. As shown in FIG. 3, the fourth component 40 is a tibial component configured to be disposed on a medial or lateral tibial plateau of a tibia T of the knee joint. The fourth component 40 includes a baseplate (or tray) 40a that is fixed to the tibia T and an insert 40b that is disposed on the baseplate 40a. The fifth component 50 is configured to be disposed on the opposite plateau of the tibia T and may be similar to or different from the fourth component 40. In this embodiment, the fifth component 50 is similar to the fourth component 40 and includes a baseplate 50a that is fixed to the tibia T and an insert 50b that is disposed on the baseplate 50a. The prosthetic device 5 may also include a patellar component (not shown).

The components of the prosthetic device 5 may be made of any material or combination of materials suitable for use in an orthopedic implant. Suitable materials include, for example, biocompatible metals (e.g., a cobalt-chromium alloy, a titanium alloy, or stainless steel); ceramics (e.g., an alumina or zirconia-based ceramic); high performance polymers (e.g., ultra-high molecular weight polyethylene); and/or a polymer composite as described in U.S. patent application Ser. No. 10/914,615, U.S. patent application Ser. No. 11/140,775, and/or International Application No. PCT/US2005/028234 (International Pub. No. WO 2006/020619), each of which is hereby incorporated by reference herein in its entirety. The prosthetic device 5 may be attached to the femur F and the tibia T using any known fixation method, such as, for example, mechanical hardware (e.g., screws) or cement. Fixation may also be accomplished via bone in-growth. To promote bone in-growth, the prosthetic device 5 may be coated with hydroxyapatite (HA), have a porous texture (e.g., beads, etc.), include one or more surfaces made from a porous metal (e.g., TRABECULAR METAL™ currently produced by Zimmer, Inc.), and/or include one or more surfaces having a cellular engineered structure (e.g., TRABECULITE™ currently produced by Tecomet).

The components of the prosthetic device 5 preferably each include at least one feature configured to provide information about the component. For purposes of explanation, a preferred embodiment is shown in FIG. 3. In this embodiment, the first component 10 includes a first feature 70a, the second component 20 includes a second feature 70b, the third component 30 includes a third feature 70c, the fourth component 40 includes a fourth feature 70d, and the fifth component 50 includes a fifth feature 70e.

The information provided by the feature may include, for example, a position, an orientation, a size, an identity (e.g., part number), and/or any other useful information regarding the component. For example, in operation, the feature can function as a reference point or datum for the component (e.g., a shape, curve, point, axis, etc.). Thus, the feature (in combination with a detection device and a computing device) may be used as a basis for calculating or determining a position and/or an orientation of the component.

The feature may be integrated with the component in any known manner. For example, the feature may be embedded in the component, affixed to the component (e.g., using adhesive), formed on a surface of the component (e.g., by etching, cutting, marking, etc.), and/or formed integrally with the component. The feature can take any of a variety of forms, some of which are described below.

The feature can be configured to be detectable (or readable) by a detection device (or detection system) using any suitable detection method. For example, the feature may be detected using optical, electromagnetic, radio, and/or acoustic methods, as are well known. As further examples, the feature may be detected using a laser scanner or infrared camera. As yet additional examples, the feature may be detected using a trackable probe or instrument in combination with an infrared camera or a mechanical arm with joint encoders. In a preferred embodiment, the detection device can read the feature after the prosthetic device 5 has been implanted in the patient and the joint has healed. Thus, for such an embodiment, an incision is not required to read the feature and information can be obtained from the feature in a non-invasive manner. For example, during a follow up visit, the surgeon can obtain information about a recently implanted prosthetic device and determine whether the position and/or orientation of the modular components of the prosthetic device are acceptable.

Some specific features and detection devices will now be described. The invention is not intended to be limited to the specific features described, nor is it intended to be limited to the described combinations of features and detection devices.

The feature may include, for example, an optical characteristic, such as an optical etching (e.g., a laser etching), an optical marking (e.g., a bar code, a checkerboard pattern, or a grid or array of dots), and/or a marker (e.g., a passive infrared marker) that can be formed or disposed on a surface of the component. Such a feature could be detected, for example, with a detection device including a laser scanner or infrared camera.

As another example, the feature can include a pattern disposed on a surface of the component. The pattern may include, for example, textures, grooves, etchings, and the like. Such a feature could be detected, for example, with a detection device that includes a trackable probe that can be slid over the pattern and an infrared camera that can detect the probe.

As another example, the feature can include a landmark or surface characteristic. The landmark or surface characteristic may be an integral or intrinsic part of the component that is sufficiently defined and identifiable to function as a recognizable marker (e.g., an articular surface, outlines of anatomical structure, shapes, colors, etc.).

As yet another example, the feature can be an interface on the component that is configured to interact with an instrument. For example, the interface could receive at least a portion of the instrument. The detection device could determine the pose of the instrument engaged with the interface, and the computing device could determine a location of the feature on the component based on the pose of the instrument. The computing device can determine the position and orientation of the component by determining the location of multiple features and knowing a geometric relationship between the features and the component.

Figure 4:
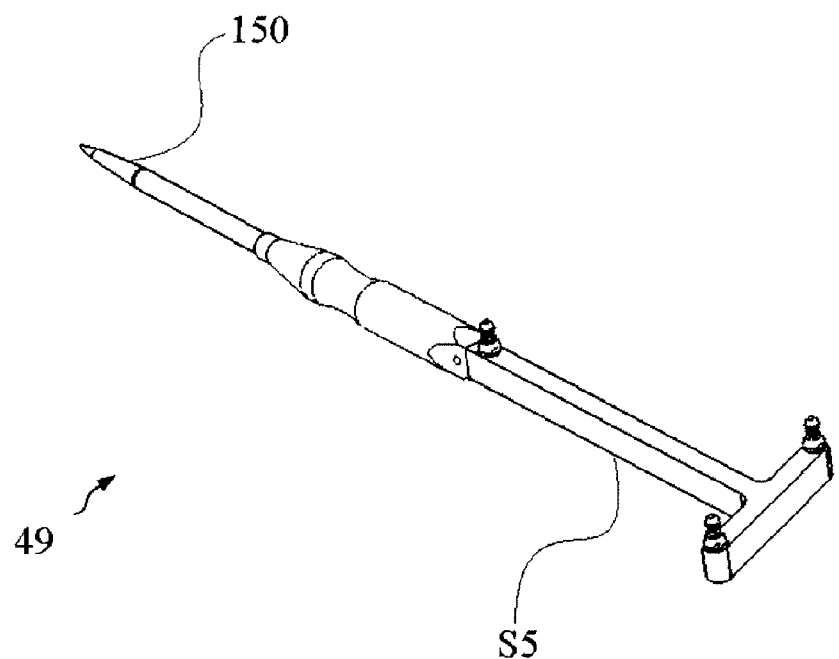
FIG. 4 is a perspective view of an embodiment of an instrument according to the present invention.
Figure 6:
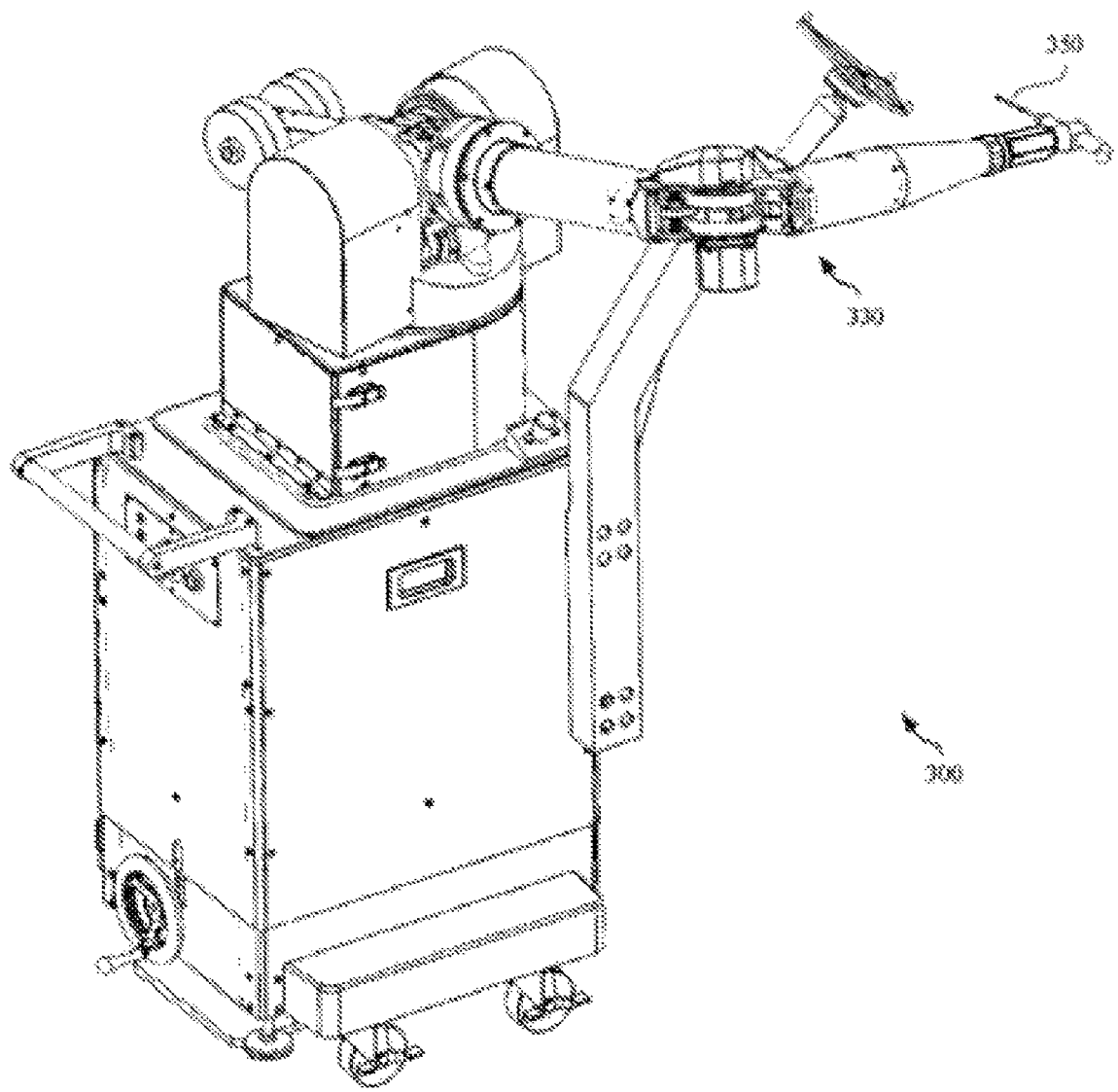
FIG. 6 is a perspective view of an embodiment of an instrument according to the present invention.

The instrument may be, for example, an instrument 49 having a probe 150 and an instrument tracker S5 as shown in FIG. 4 and described in a U.S. patent application Ser. No. 11/357,197 titled "Haptic Guidance System and Method," filed Feb. 21, 2006, and hereby incorporated by reference herein in its entirety. The instrument tracker S5 can include an array of markers (e.g., reflective spheres) detectable by a detection device (including, e.g., an infrared camera) and having a unique geometric arrangement and a known geometric relationship to the probe 150. The known geometric relationship may be, for example, a predefined geometric relationship between the array of markers and an endpoint and an axis of the probe 150. Knowing the position and orientation (i.e., pose) of the tracker S5 and the geometric relationship between the tracker S5 and the probe 150, a computing device can calculate or determine the pose of the probe 150. In one embodiment, the instrument includes a probe disposed on a mechanical tracking arm as described in U.S. Pat. Nos. 6,033,415 and/or 6,322,567, each of which is hereby incorporated by reference herein in its entirety. In another embodiment, the instrument includes a haptic device 300 having a robotic arm 330 with a tool 350 as shown in FIG. 6 and described in the U.S. patent application Ser. No. 11/357,197 titled "Haptic Guidance System and Method," filed Feb. 21, 2006. The robotic arm 330 includes joint encoders to enable a computing device to determine a pose of the tool 350.

Figure 5:
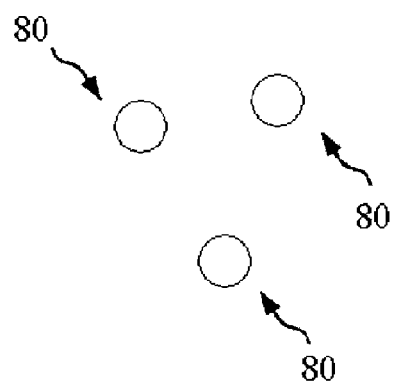
FIG. 5 is a plan view of an embodiment of an interface according to the present invention.

The interface can be configured to receive at least a portion of the instrument. For example, as shown in FIG. 5, the interface may include one or more divots 80 disposed on a surface of the component and into which the user can insert a tip of the instrument. The detection device can then acquire pose data for the instrument, and the computing device can determine a location of the divot by determining a location of the tip of the instrument. Determining the location of three divots enables the computing device to define a plane, which defines a position and orientation of the feature. Knowing the position and orientation of the feature and a geometric relationship between the feature and the component, enables the computing device to determine the position and orientation of the component. In this manner, the feature is configured to provide information about the component. Alternately or in addition to a divot, the interface may include one or more surfaces (e.g., flat or contoured) on which a similarly shaped probe (e.g., a probe having a flat or contoured tip) or trackable mechanical jig may be disposed.

Figure 7:
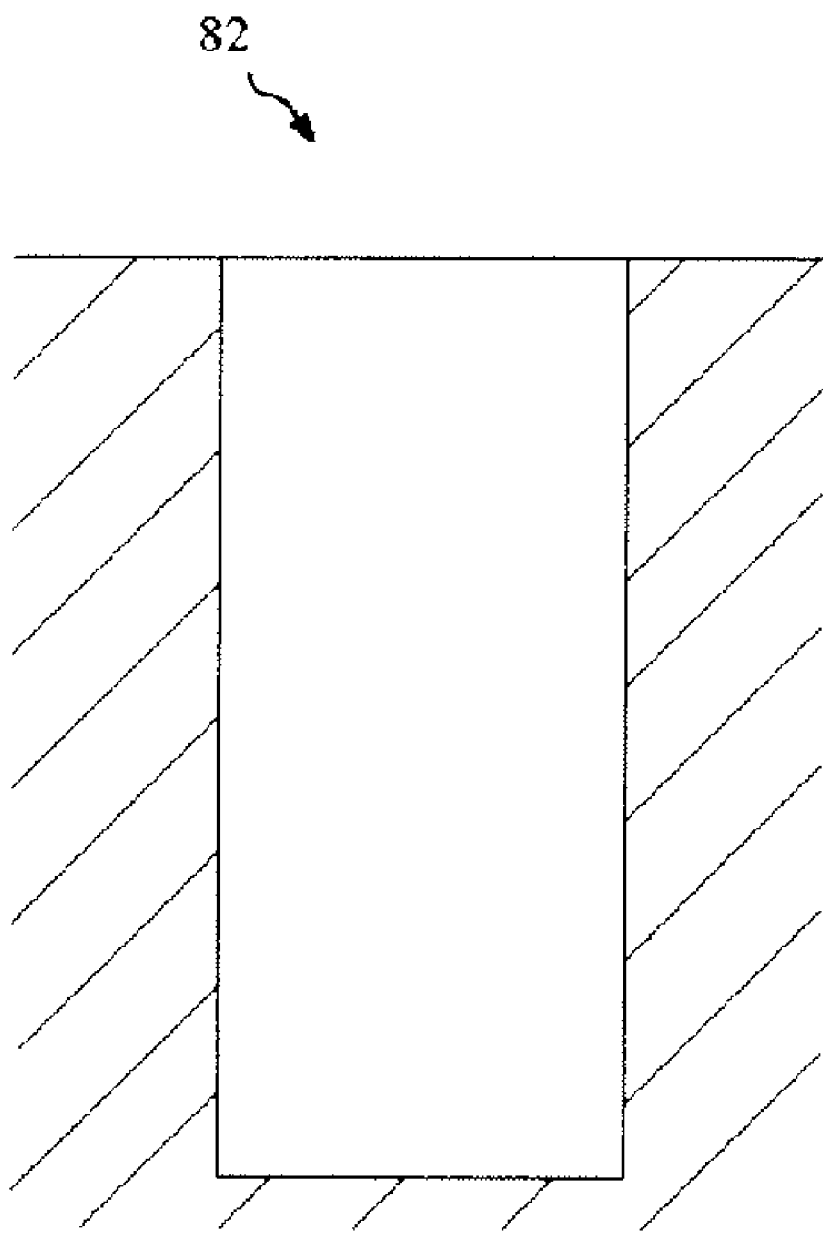
FIG. 7 is a cross sectional view of an embodiment of an interface according to the present invention.

In one embodiment, the interface includes a cavity 82 (shown in FIG. 7) into which a tip of the instrument may be inserted. The cavity 82 may be, for example, a cylindrical cavity. When the instrument is inserted in the cavity, an axis of the feature may be determined. If the instrument is prevented from rotating in the cavity, a third constraint is established so that the computing device can calculate the position and orientation of the feature and ultimately of the component. The instrument may be prevented from rotating in any known manner. For example, at least a portion of the cavity 82 may have a shape (e.g., a triangular shape, a rectangular shape, etc.) that is keyed to a shape of at least a portion of the instrument shaft so that the instrument is locked in place when inserted into the cavity.

As yet another example, the feature may be a structure that emits one or more signals that provide information. The feature may, for example, emit a directional signal having a known orientation relative to the component. Such a directional signal allows for determining the location and/or orientation of the component. A structure that could be used to provide such a directional signal includes, for example, a transmitter positioned on the edge of the implant. A detection device that could be used to detect the directional signal includes, for example, a receiver capable of triangulating and identifying a position. As another example, the signal emitting structure may include at least one sensor. The sensor may be, for example, a smart label such as a passive radio frequency identification (RFID) tag. The RFID tag is affixed to the surface of the component and/or embedded in the component and is detectable by an RFID reader that emits radio waves. As a user scans the component with the RFID reader, the radio waves power the RFID tag, which then communicates with the RFID reader. For example, a RFID reader may consist of two readers at a known distance apart. A component may have three or four RFID tags embedded in the component at known relative positions. The readers send out a signal to excite the component tag and the readers measure the time it takes for the signal to return. Each reader is then able to compute the location of the component tag. This is repeated sequentially for all tags in the component, all within a fraction of a second. Once the location of all the tags in the component are known, the pose of the implant is known. One advantage of using a signal emitting structure is that the detection device can obtain information from the structure even when the prosthetic device 5 is not visible or exposed (e.g., when the prosthetic device 5 is covered with tissue such as muscle and skin). As a result, the signal emitting structure can provide information about the component after the component has been implanted and the patient's joint has healed. Thus, the component can be monitored in a non-invasive manner at any time during the life of the component.

As yet another example, the feature may include one or more piezoelectric transducers embedded in the component. A piezoelectric measuring system then can be used to measure piezoelectric voltages generated in response to deflections of the component. In the case of a joint having tibial and femoral components, a particular stress and deflection pattern exists in the tibial component due to forces applied by the femoral component during normal joint operation. This deflection pattern will correspond to a voltage pattern generated as a result of movement of the piezoelectric transducers caused by the forces applied by the femoral component. For a new tibial component, this voltage pattern may be characterized as a "no wear" voltage pattern and can be predicted and/or experimentally measured. Over time, as the tibial component experiences wear, the deflection pattern of the tibial component will change. This wear may be manifested, for example, as a reduction in thickness and/or material properties of the tibial component. As the deflection pattern changes, the corresponding voltage pattern generated by the piezoelectric transducers will change. Differences in the voltage pattern over time can be detected and used to quantify wear of the tibial component.

The ability to communicate information from the component via the feature and the detection device provides a wide variety of capabilities. For example, if the feature provides information to the detection device regarding the position and/or orientation of the feature, a computing device can calculate or determine the position and/or orientation of the component based on that information and a known geometric relationship between the feature and the component.

The ability to determine the position of the component makes it possible to determine the positioning of the component relative to another component and/or relative to a plurality of other components. In an instance where the components are, for example, all parts of a prosthetic device configured to be disposed or implanted in a joint, the present invention can provide an improved ability to position those components relative to one another. In the instance where at least one of the components is the patient's bone disposed in the joint (e.g., femur, tibia, or patella), the present invention can provide an improved ability to position the component of the prosthetic device relative to the bone component. In such an instance, the feature on the bone component may be, for example, its shape, contour, correspondence point(s), and/or a virtual feature from a model of the bone.

The positioning can be achieved in a variety of ways. For example, when two or more components each include a feature, the computing device can calculate or determine a desired position and orientation of the components relative to one another (geometric relationship(s)). During a surgical procedure, the computing device (in combination with the detection device), can determine the actual geometric relationship(s) of the components and then compare the actual relationship(s) of the components to the desired geometric relationship(s). If the actual relationships deviate from the desired relationships, one or more of the components can be repositioned or adjusted during the surgical procedure to achieve the desired relationships.

The computing device (or computer) may be any suitable computer, such as, for example, a computer aided surgery (CAS) or surgical navigation system. In a preferred embodiment, the computing device is a haptic guidance system as described in a U.S. patent application Ser. No. 11/357,197 titled "Haptic Guidance System and Method," filed Feb. 21, 2006, and hereby incorporated by reference herein in its entirety.

The computing device can determine or create the desired geometric relationship in a variety of ways. For example, the computing device can implement finite element analysis (FEA) to provide performance feedback on the relationships between the components (two, three, or more). For example FEA may be used to calculate the predicted stresses on components. Based on the results of FEA, the computing device can be used to modify the relationships between the components until the predicted stresses fall within acceptable levels (i.e., the desired geometric relationship). As another way to determine the desired geometric relationship, the computing device can reference an existing database of configurations to create the relationships between the plurality of components. The desired relationship also may be based, for example, on an image dataset, an imageless dataset, an equation, a tolerance, a geometric model, data representative of a patient's anatomy (e.g., preoperative CT image data, ultrasound data), a virtual (or haptic) object associated with (or registered to) the anatomy, a parameter relative to the anatomy (e.g., a depth defined with respect to a portion of the anatomy); and/or the like.

According to one embodiment, a system for implanting the prosthetic device 5 includes the first component 10 having the first feature 70a and the second component 20 having the second feature 70b (as shown in FIG. 3). The computing device (or computer) can be programmed to determine a desired geometric relationship between the first component 10 and the second component 20 based at least in part on the first feature 70a and the second feature 70b.

In operation, the computing device (e.g., a CAS system) is configured to determine a pose (i.e., position and orientation) of one or more components of the prosthetic device 5 with respect to a coordinate frame of reference during a surgical procedure and/or after implantation of the components (e.g., as described above). The coordinate frame of reference of the components can then be registered to (mapped to or associated with) a coordinate frame of reference of interest to achieve spatial alignment or correspondence between the coordinate frames (e.g., using a coordinate transformation process as is well known). The coordinate frame of reference of interest may be any suitable coordinate system, such as a coordinate system being used by a process running on the CAS system, a coordinate system of the patient's anatomy, and/or the like. For example, component pose data can be registered to a representation (or image) of the anatomy, a geometric model representing a desired geometric relationship between the anatomy and the components, and/or a geometric model representing a desired geometric relationship among the components. Using the registration data, the system can determine, for example, (a) a spatial relationship between the image of the anatomy and the components of the prosthetic device 5 and (b) relative spatial relationships among the various components of the prosthetic device 5. Using this information, the surgeon can then adjust one or more of the components to achieve the desired relationships.

The desired geometric relationship may be determined before or during a surgical procedure, and the first component 10 and second component 20 can be manipulated relative to one another during the surgical procedure until the desired geometric relationship is achieved.

For example, prior to preparing the bone surfaces, the surgeon can determine where to place each of multiple components and the consequences of those placements. As a specific example, the first component could be the medial femoral unicondylar and the second component could be the patello-femoral piece. The desired relationship between the two components could be that their articular surfaces near the transition zone be tangent. This would ensure the patella would transition from one component to another without major increases in stress or force. The computer would predict the performance based on this placement, providing feedback to the surgeon so that he/she can make appropriate adjustments.

As another example, during orthopedic surgery, a surgeon can register an existing component in the joint (e.g., the first component 10 having the first feature 70a or the patients bone). The existing component may be, for example, a trial implant, a newly installed component, or an existing implant from a previous surgery. Based on the registration (which includes information from the first feature 70a regarding a position and orientation of the existing component), the surgeon can prepare the bone to receive a new component (e.g., the second component 20 having the second feature 70b) so that, when the new component is installed, the new and existing components have a predetermined desired geometric relationship. The surgeon can also verify the installation by registering the existing and newly installed components to confirm that the desired relationship has been achieved. As a result, the surgeon has the ability to build the implant in the joint so that the implant components have relative positions designed to maintain implant life and natural patient biomechanics. This capability is advantageous both during initial implantation of the prosthetic device 5 and during revision surgery. For example, during a revision surgery, rather than replacing an entire existing prosthetic device 5, the surgeon can leave existing components that are in good shape in place and add new components as necessary to replace worn components and/or resurface newly diseased areas.

In operation, a surgical method according to an embodiment of the present invention includes the following steps. In step S1, information is acquired about a first implant (e.g., the first component 10) disposed in a joint. In step S2, information is acquired about a second implant (e.g., the second component 20) disposed in the joint. As described above, the information may be acquired, for example, by contacting at least a portion of the implant with a trackable instrument and/or scanning at least a portion of the implant with a detection device. In step S3, a relationship between the first implant and the second implant is determined based on the information acquired about the first and second implants. In step S4, the determined relationship is compared to a desired relationship. In step S5, if the determined relationship deviates from the desired relationship, one or both of the implants is adjusted to achieve the desired relationship. The acquired information about the first and second implants may also be used to determine a rate of wear of the first and second implants. Additional steps include, for example, applying a force to the joint when the information about the first implant and the information about the second implant are acquired and determining a condition of soft tissue in the joint based at least in part on the information acquired about the first and second implants.

According to another embodiment, a surgical method according to the present invention includes the following steps. In step S101, information is acquired about a first implant (e.g., the first component 10) disposed in a joint. In step S102, placement in the joint of a second implant (e.g., the second component 20) is planned based at least in part on the information acquired about the first implant and a desired relationship between the first implant and the second implant. In step S103, the second implant is positioned in the joint. In step S104, information is acquired about the second implant when the second implant is disposed in the joint. In step S105, a relationship between the first implant and the second implant is determined base on the information acquired about the first implant and the information acquired about the second implant. In step S106, the determined relationship is compared to the desired relationship. In step S106, the first implant and/or the second implant is adjusted to achieve the desired relationship.

Figure 8:
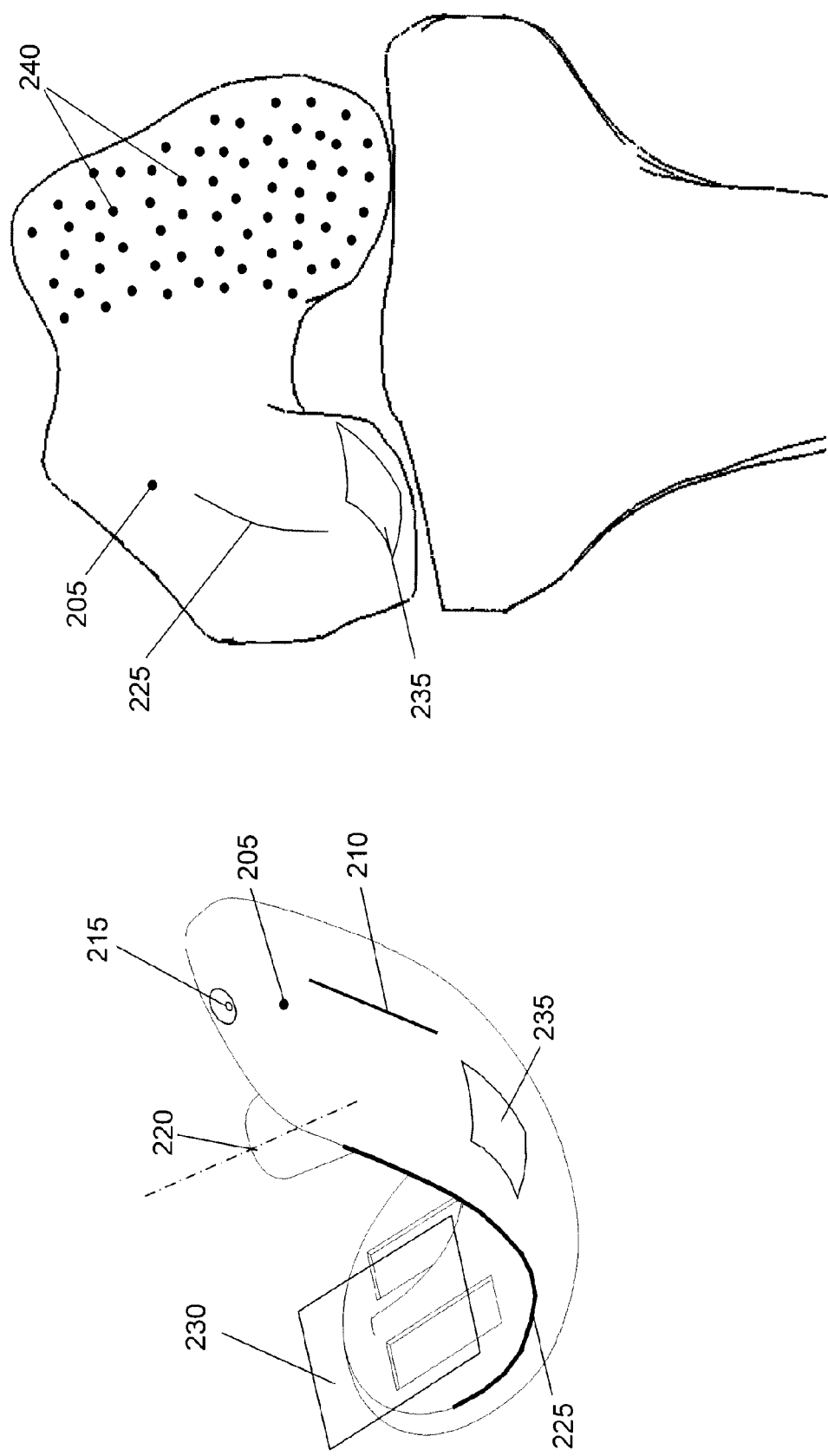
FIG. 8 is a perspective view of an embodiment of a prosthetic device and a patient's anatomy according to the present invention.

According to one embodiment, the relative positions of the two or more components, which can comprise the prosthetic device 5 and/or the relative position of the anatomy of the patient (i.e., the implant joint), can be determined by acquiring the features of the two or more components. The feature may be, for example, one of a line, length, arc center, radius, plane, an anatomic location, soft tissue insertion/attachment point, virtual feature or correspondence point 240. As shown in FIG. 8, a virtual feature (visible via a computer-generated model) may be a point 205, line 210, divot 215, axis 220, curve 225, plane 230 or surface 235 that is not necessarily physically located on an actual component, but may have been used, for example, to construct a component. FIG. 8 also illustrates the use of correspondence points 240 for a patient's anatomy. Correspondence points 240 of a patient's anatomy are unique points that are the same relative point from bone to bone of different patients regardless of the bone shape or size. For example, suppose the most anterior aspect of the lateral cortex of a femur is identified as a correspondence point. Then, that location would correspond to the same location on another femur regardless of the femur shape or size.

The features of a prosthetic device 5 and/or a patient's anatomy may be acquired using several acquisition methods. For example, imaging techniques may be used to obtain an image dataset of the features, or the computing device may acquire an imageless dataset of the features. Laser probing, ultrasound probing, physical instrument probing, RFID detection, CAD modeling and or other sensor techniques may also be used to acquire features of a prosthetic device 5 and/or patient's anatomy. Once the features are acquired, the computing device can then determine and modify the relationships between the identified features.

For example, FIG. 9(a) is a representation of the features, i.e., correspondence points 240 of a femur F acquired via a CT scan. FIG. 9(b) is a visual representation of the features, i.e., points 205 of a medial unicondylar or PFJ modular component acquired with a CAD modeling acquisition method. FIG. 9(c) is a visual representation of the computing device acquiring the relationship between the features of the modular component shown in FIG. 9(b) and the femur F shown in FIG. 9(a). In FIG. 9(c) the relationship that is determined is the minimum distance between the implant features and the femur F correspondence points. In this embodiment, the predicted performance determined by the computing device is the anatomic fit of the implant and femur F. In one embodiment, the computing device uses a least squares method to determine the best anatomic fit between the implant and femur F. Based on the anatomic fit values, a surgeon may then modify the size and orientation of the modular components to obtain a desired anatomic fit.

The patient's anatomy that will receive an implant may have several virtual features 200. For example, the most distal, most anterior, or most posterior locations on a medial or lateral articular surface of a bone B may be stored by the computing device as virtual features 200. These virtual features 200 are shown, for example as points 1-6 in FIG. 12(c). In addition, the anterior sulcus or distal sulcus of a tochlear groove (points 7 and 8 in FIG. 12(c)) and the most prominent medial and lateral locations (epicondyles) (points 9 and 10 in FIG. 12(c)) may be virtual features 200. Other virtual features 200 for joints may include but are not limited to the mechanical axis of the femur F or tibia T, Leo's (Whiteside's) line or AP (anterior-posterior) axis, the epicondylar axis of the femur F, the sulcus pathway of the trochlear groove, the highpoint pathway of the articular surfaces and the trace line on the femur of the contact point between the tibia and the femur throughout the range of motion.

In addition, there are numerous other features of components and the patient's anatomy that can be acquired and modified. For example, given a femoral unicondylar implant having a feature of the articular surface and a patello-femoral implant having a feature of the articular surface, the computing device may be configured to determine the tangency of the implants' articulating surfaces and modify the tangency based on patella stress during the transition from the femoral unicondylar implant to the patello-femoral implant. In the alternative, given a femoral unicondylar implant having a feature of a set of points on the articular surface and a femur having a feature of a set of correspondence points, the computing device may be configured to determine the minimum distance between the set of points on the articular surface of the femoral unicondylar implant and the correspondence points on the femur and modify the minimum distance based on the anatomic fit between the femoral unicondylar implant and the femur. Further, given a tibial trial with a feature being the trial's most anterior point and a femoral unicondylar trial having a feature of set points, the computing device may be configured to determine the orientation of the femoral unicondylar trial along the set points and modify the pose of the components based on the predicted wear (determined from a lookup table for the pose of the tibial trial with respect to the pose of the femoral unicondylar trial).

Figure 15:
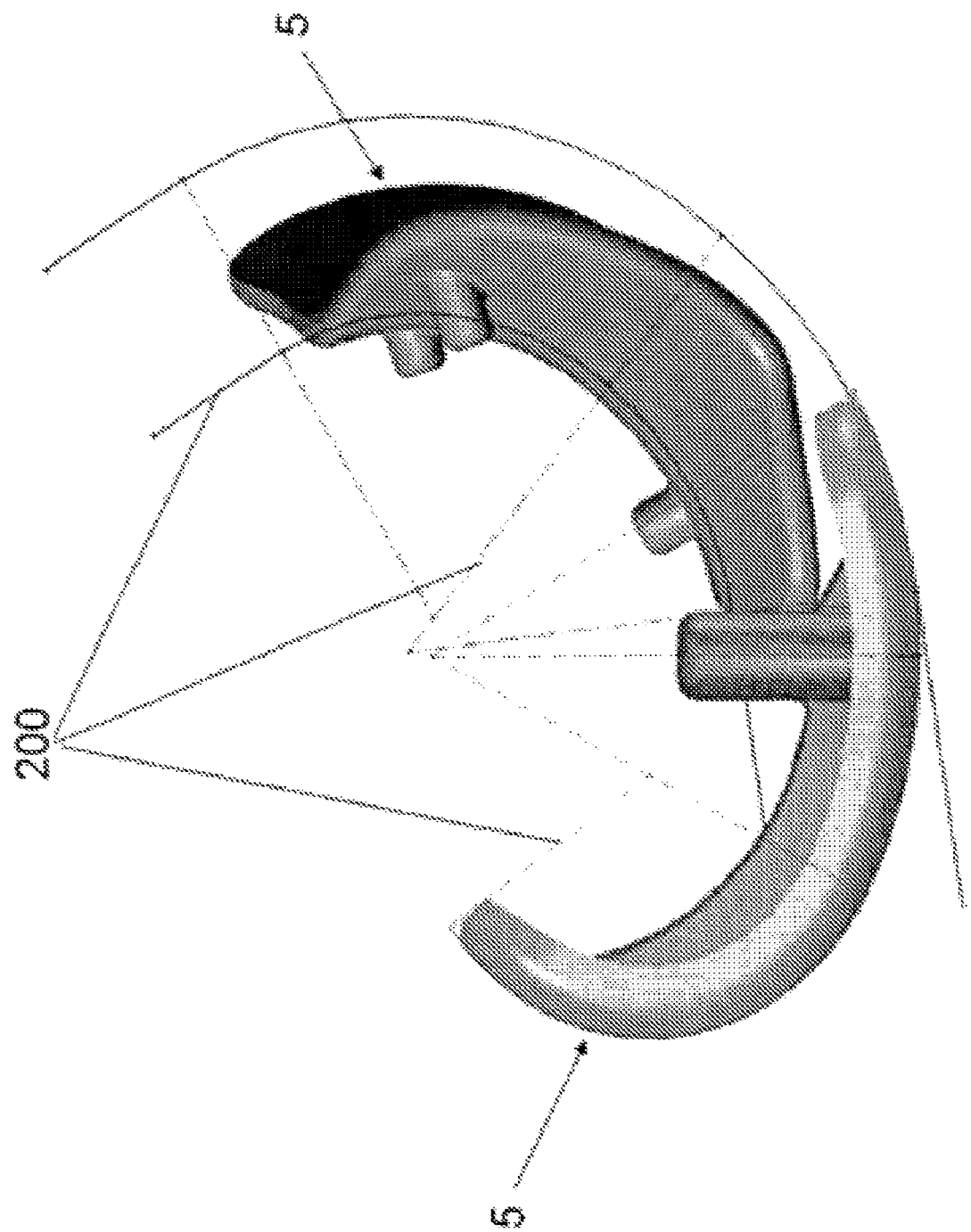
FIG. 15 is a plan view of an embodiment of two prosthetic device components according to the present invention.

Once the virtual features of the desired prosthetic device 5 and patient's anatomy are captured, according to another embodiment, the computing device is programmed to establish or create a relationship between the virtual features 200. This relationship may be a component-to-component relationship or a component-to-joint relationship. For example, as shown in FIG. 13(a), the computing device fits the bone j-curve of a modeled bone B to that of a prosthetic device 5 component's sweep curve by a least squares method. In the alternative, as shown in FIGS. 14-15, the computing device can position the femoral unicondylar and patello-femoral component so that they are tangent to one another. Relationships may also be established by making the arc centers of a prosthetic device 5 and bone B model coincident or by selecting a prosthetic device 5 component that has a radii that most closely matches the radii of a bone.

Other relationships that may be established by the computing device include positioning the axis of a femoral unicondylar peg in parallel with the mechanical axis of a femur, positioning the center plane of a femoral unicondylar fin in parallel with a mechanical axis of a femur, positioning an articular surface of an implant component so that it is tangent to an articular surface of a bone, positioning an articular surface of an implant so that it is offset from an articular surface of a bone, aligning a patello-femoral joint component sulcus path with a patella center trace line, aligning a femoral unicondylar low point pathway (guide curve pathway) with a tibia contact point trace line and adjusting the distance between a femoral unicondylar anterior tip and the termination of the patello-femoral articulating surface.

According to one embodiment, the computing device (or computer) is programmed to determine a relationship between two or more components of the prosthetic device 5, each having a feature, and is further programmed to provide feedback on the performance and/or predicted performance of the components based on the relationship. If the performance or predicted performance values deviate from desired values, the relationship between the components can be modified to obtain a desired performance and/or predicted performance. Further, the computing device is programmed to determine the relationship between the prosthetic device 5 and the anatomy of the patient, and provide feedback on the performance and/or the predicted performance of the prosthetic device 5 based on the relationship between the prosthetic device 5 and the anatomy of the patient. If the performance or predicted performance values deviate from desired values, the relationship between the prosthetic device 5 and the anatomy of the patient can be modified to obtain a desired performance and/or predicted performance.

Performance and predicted performance may be related to any number of conditions that can characterize the operational ability of the prosthetic device 5. For example, performance and predicted performance may be related to wear, stress, kinematics, kinetics, range of motion (ROM), fixation strength, ligament balance, anatomic fit, fixation shear force and longevity of the prosthetic device 5. Other predicted performance values include but are not limited to polyethylene wear ($mm^3$ per million cycles), tibiofemoral and patellofemoral kinematics throughout the range of motion (e.g., maximum flexion, internal/external tibial or femoral rotation, patella flexion and tilt, femoral rollback), quadriceps force (i.e., an indication of knee efficiency), ligament force during a range of motion. Kinematics is related to the motion of a body. For example, kinematics relates to AP translation, rollback, internal and external rotation, flexion, patella tilt, patella spin, etc. Kinetics relates to forces and/or moments acting on a body such as compressive force, shear force, torque, anterior/posterior (AP) force, medial/lateral (ML) force and flexion moment.

Figure 10B:
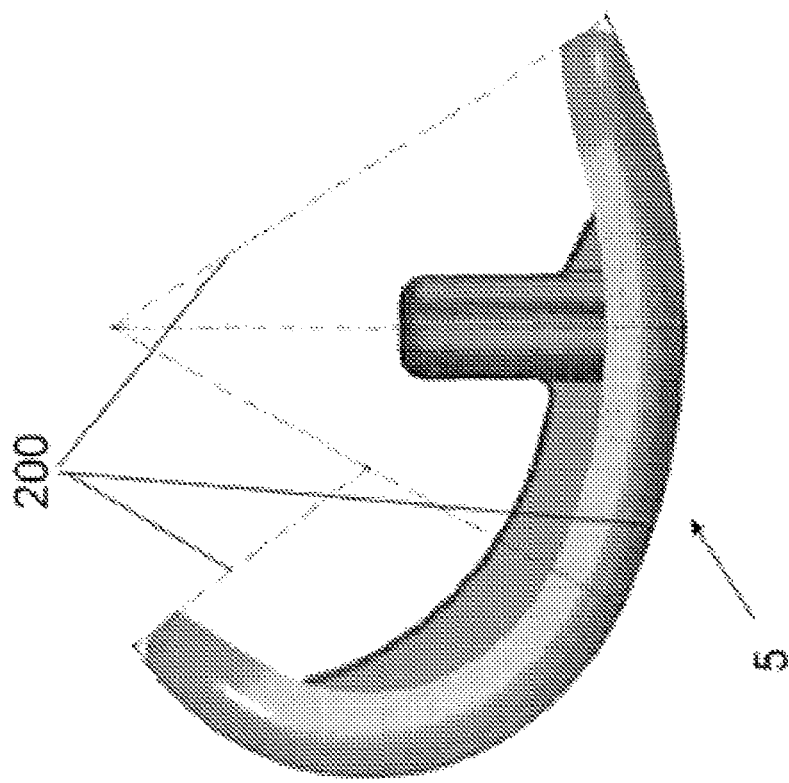
Figure 10A:
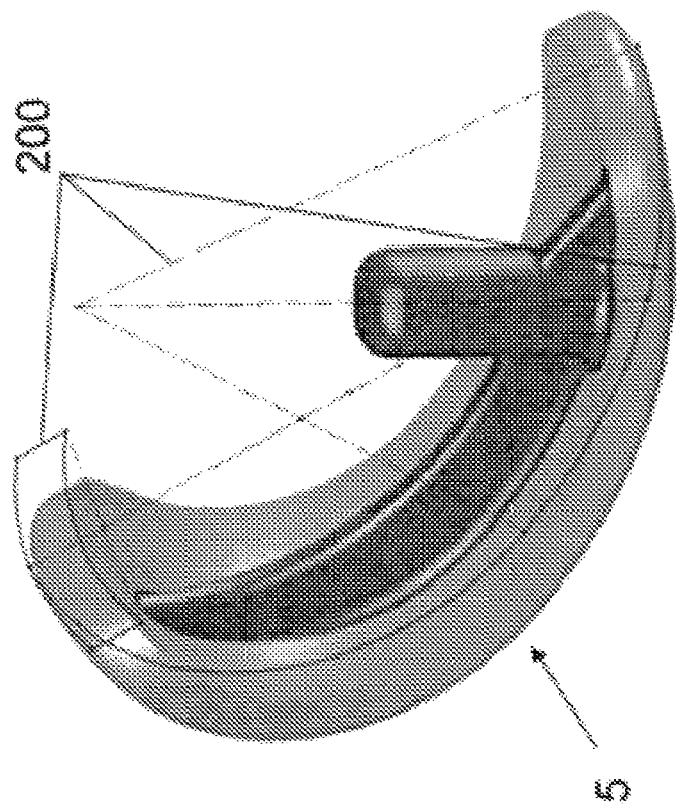

According to one embodiment, the computing device (or computer, e.g., a computer aided design (CAD) system using SolidWorks, Unigraphic, Pro/E or similar programs) is programmed to generate virtual 3D models of the prosthetic devices 5 that will be implanted into a patient. FIGS. 10(a)-10(d) illustrate a CAD model of a prosthetic device 5 to be implanted near the coronal articular cross section of a bone. The computing device constructs the CAD model by capturing profiles representing the coronal articular cross section of a bone through a guide curve pathway. The profiles can also be revolved about a predetermined arc center, axis or series of axes and captured for modeling purposes. The guide curves used to model the implant may be planar but are preferably three-dimensional in order to capture the complex shape of the bone. The construction geometries, i.e., the profiles, guide curves, arc centers and axes are stored by the computing device as virtual features 200. As described above, virtual features 200 may be any feature, point, line, arc, radii, plane, etc., that can be created and stored in a CAD model. In addition, as shown in FIGS. 10(a)-10(c), a prosthetic device 5 may have several other virtual features. For example, the point at which a guide curve exits a femoral unicondylar CAD model anteriorly (the anterior tip) or posteriorly (max flexion) can be used as a virtual feature. In addition, the center plane of the fin, the plane of any flat feature, the axis of peg(s), the most distal or most posterior point or the medial low point of the tibia may be used as virtual features 200.

As described above, these virtual features will be used by the computing device to determine component-to-component and component-to-joint relationships as well as predicted performance characteristics. To acquire the virtual features of a stored CAD component model, the computing device makes the virtual construction geometry of the component temporarily visible. FIGS. 10(a)-10(c) show a prosthetic device 5 and the device's virtual features. FIG. 10(d) shows the prosthetic device 5 without its virtual features identified. A CAD model of a patello-femoral joint 1100 created in the manner described above is shown in FIG. 11(a) and 11(b).

Figure 12C:
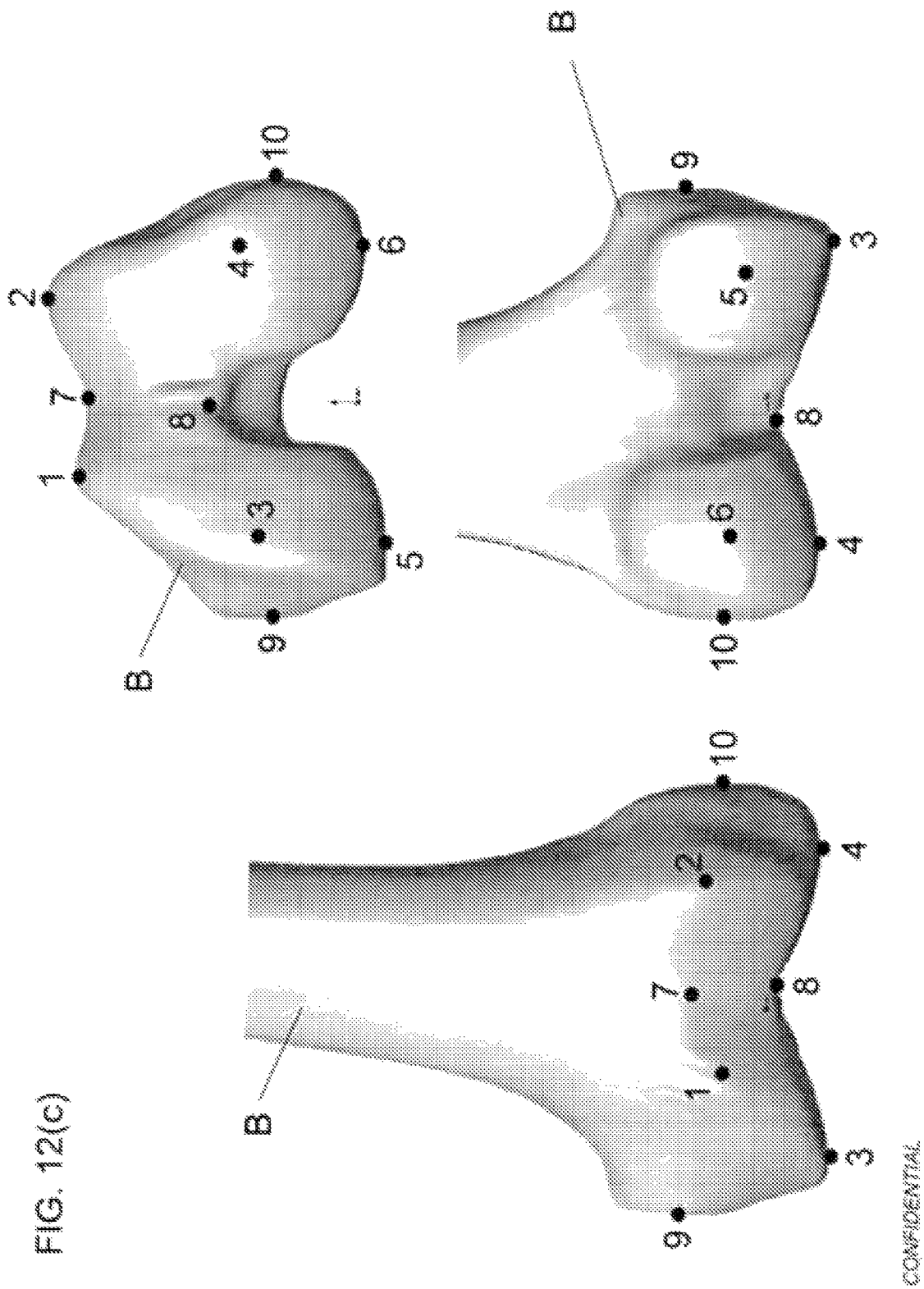

According to another embodiment, and as shown in FIGS. 12(a)-12(c), the computing device is programmed to generate models of the patient's anatomy, i.e., joints or bones B that will be implanted with a prosthetic device 5. The computing device may be programmed to characterize the shape of a bone or soft tissue such as computing the ideal sagittal curve geometry and the respective radii and arc centers. For example, the bone B in FIGS. 12(a)-12(b) have a posterior arc radius of 22 mm, a distal arc radius of 44 mm and an angular transition between these 2 radii of 27 degrees, These representative geometric features may be stored by the computing device as virtual features 200. In order to obtain the virtual features 200 of the patient's anatomy, according to one embodiment, a CT scan of the patient's anatomy is loaded into the computing device. The computing device is configured to execute anatomy characterization software that acquires the virtual features 200 from the CT scan. According to another embodiment the virtual features of the patient's anatomy may be obtained by, for example tracing the contact point between the tibia T and the femur F onto the femur F throughout the range of motion or tracing the track of a patella onto a femur F throughout the range of motion. As described above, these virtual features will be used by the computing device to determine component-to-joint relationships as well as predicted performance characteristics.

According to one embodiment, the computing device is programmed to determine the predicted performance of a modeled system for implanting a prosthetic device 5. As described above, the anatomic fit of a prosthetic device 5 is an example of predicted performance. Generally, the computing device is programmed to use acquired virtual features 200 to conduct various computational simulations on a prosthetic device system (e.g., a knee implant) to obtain the predicted performance of the system.

Predicted performance may be represented in several different ways. For example, predicted performance may be a numerical value that represents how well a component fits with a joint (anatomic fit). Given FIGS. 13(a)-13(b), the computing device may determine anatomic fit by, for example, comparing the radii of the component to the radii of the bone. Alternatively, the computing device may use the least squares value of the component/bone system shown in FIGS. 13(a)-13(b) to determine the value of the anatomic fit (predicted performance).

Generally, the computer will virtually implant a prosthetic device 5 onto a bone B or joint in an ideal pose (e.g., when all the articular surfaces of the femoral implant components are tangent). Based on the ideal pose, the computing device obtains baseline information (either by performing a functional activity simulation, such as a deep knee bend or by obtaining the information from a lookup table of previously performed simulations of particular poses) such as force limitations, as well as wear and stress limitations of the prosthetic device 5. In the alternative, the prosthetic device 5 may be virtually implanted in less than ideal poses so that the computing device can determine what the affect of non-ideal prosthetic device 5 placement is on the prosthetic device's 5 performance and the patient's health. For example, the computing device may perform a sensitivity analysis on a virtually implanted prosthetic device 5 by simulating a parametric matrix of malpositioning, misalignment and varying size compatibility permutations. According to another embodiment, in an instance where the position of a first component is suboptimal, the computing device is programmed to suggest the optimal relationship and placement of one or more additional components in relationship to the first component. The performance characteristics (i.e., kinematic and kinetic values, wear and stress) of the non-ideally positioned prosthetic device 5 implant components may be compared with the characteristics of the ideally placed implant components to create predicted performance values that will be used as pre-operation data by pre-operation programs of the computing device. According to another embodiment, the computing device is programmed to populate a lookup table with the acquired predicted performance values. Accordingly, when the ideal pose of one or more components is modified, if the modified position has been previously simulated, the computing device locates the modified pose in the lookup table to obtain the predicted performance data. The lookup table is advantageous because it provides instant feedback as opposed to simulating a modification. which may take hours to complete.

According to one embodiment, the computing device is configured to communicate/display the predicted performance values for a given component placement to a user/surgeon. This information may be displayed in any number of visual formats including text, charts, tables, matrices, diagrams, etc. According to one embodiment, the predicted performance information is presented so that the surgeon can compare the performance values of an ideal implant component positioning to that of a modified positioning. For example, the predicted performance information may reveal how the modified positioning of an implant component will cause a 30% increase in patella shear stress, a 50% increase in patella wear and a 40% decrease in patella fixation strength. Thus, the predicted performance information allows a surgeon to make iterative changes to the positioning of the implant components until acceptable performance values are obtained.

Figure 16:
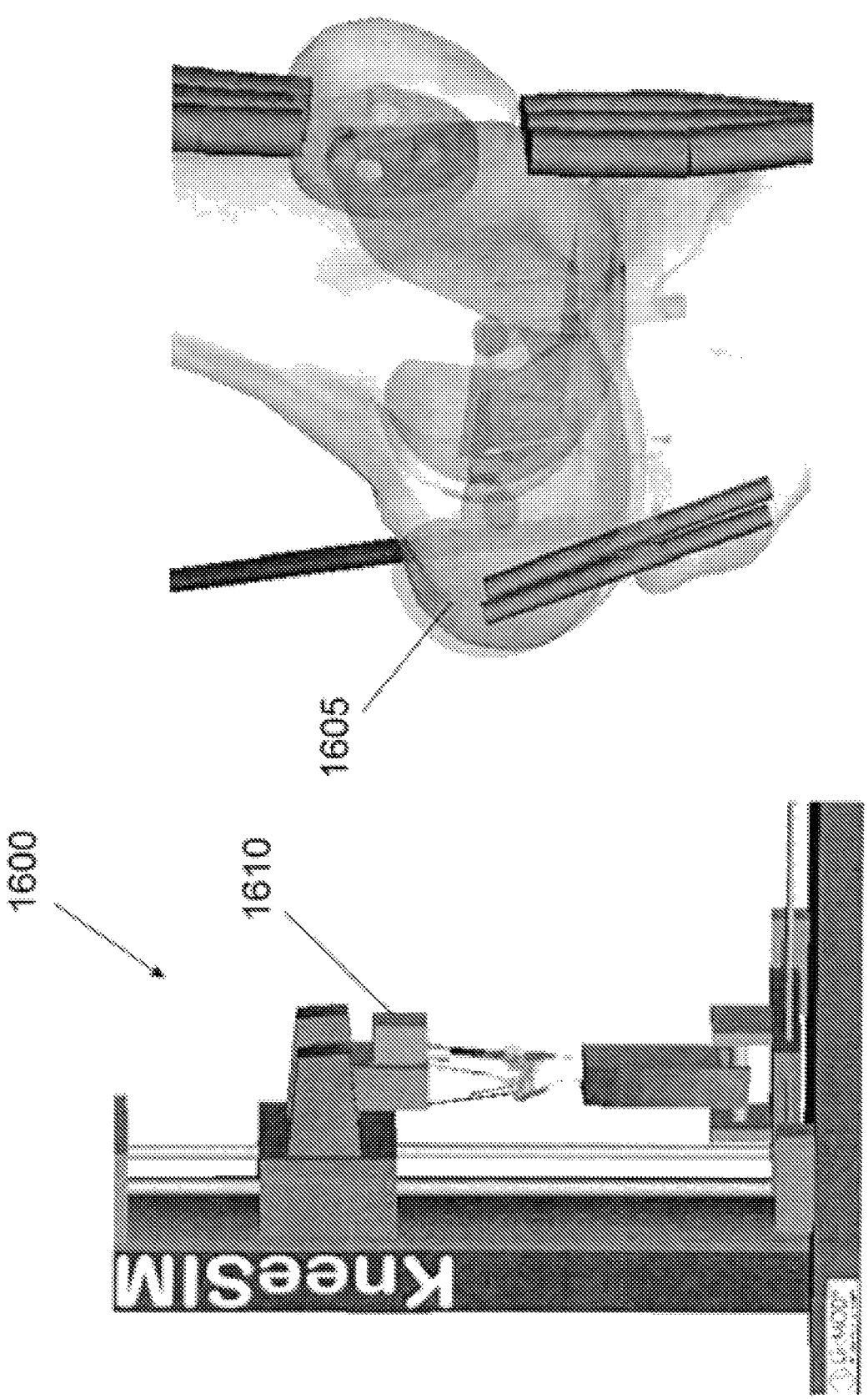
FIG. 16 is a perspective view of an embodiment of a prosthetic device simulation according to the present invention.

FIG. 16 shows an example of a computational simulation (KneeSIM) 1600 used to determine the predicted performance of a modular knee implant 1605. The simulation shown in FIG. 16 is a 3D, dynamic, physics-based system that simulates in vivo functional activities for the purpose of evaluating the kinematic and kinetic performance of knee implant designs. In the computational simulation, component models are virtually implanted onto a lower-leg, Oxford rig-like knee simulator 1610. The simulator 1610 has active quadriceps and hamstring actuators. Surrounding soft tissues such as the LCL, MCL and capsule are also modeled. The knee simulator 1610 performs activities such as a normal gait, a deep knee bend and a lunge. During the simulation activities, the computing device obtains data related to the kinematic and kinetic information of the bones, components and soft tissues.

According to one embodiment, the computational simulation is used to predict long-term wear on the implanted components and the joints. According to one embodiment, all simulations for every conceivable pose and component size mismatch is performed prior to releasing the system to the public. The results of the simulations can be stored on a computing device such that when components are placed in a certain pose, the predicted performance values can be displayed to a user. For example, according to one embodiment, the computational simulation uses finite element analysis to analyze the knee implant 1605. In this embodiment, modeled components are virtually implanted onto a joint simulator.

Here a standard kinematic or kinetic activity pattern is used to manipulate the knee simulator 1610, and predicted performance information is extracted. According to another embodiment, the computational simulation is used to predict the performance of a prosthetic implant based on the distance between a femoral unicondylar anterior tip and an edge of a patello-femoral articulate surface. The distance between these two anatomic points may indicate the amount of wear and stress that will be placed on attached implant components. For example, if the distance between the two anatomic points is relatively small the patella will likely be able to transfer from one implant component to another very smoothly which will in turn decrease the wear and tear on the implant components.

Figure 17:
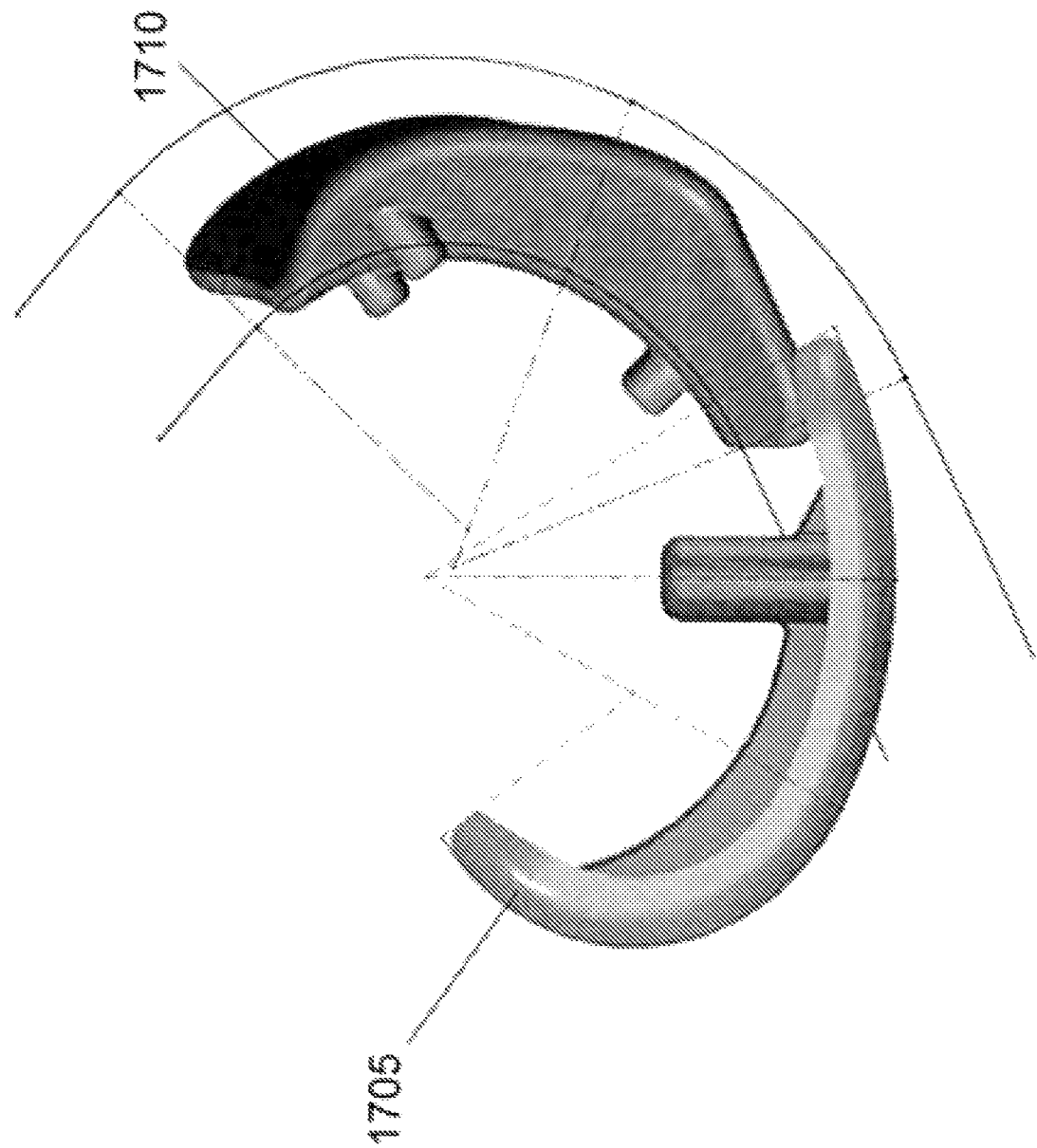
FIG. 17 is a perspective view of an embodiment of two prosthetic device components according to the present invention.

According to another embodiment and as shown in FIG. 17 the computational simulation can determine predicted performance values if the articular surfaces of the femoral unicondylar 1705 and patello-femoral joint 1710 are not tangent. Generally, in this orientation, the patella's shear stress during transition from one component to another is increased. The computing system presents this information to a surgeon which in turn may modify the positioning of the components to decrease the patella shear stress predicted during the computational simulation.

The computational simulation is also configured to determine if the femoral unicondylar is not aligned with the tibia contact trace line. In this embodiment, the computational simulation will likely show that given this configuration the fixation strength of the components and the kinematics of the knee are compromised. Again, the computing system presents this information to a surgeon which in turn may modify the positioning of the components to obtain more acceptable performance values than those predicted during the initial computational simulation.

According to one embodiment, in a surgical method according to the present invention, the relationship between the first implant and the second implant is modified based on a performance characteristic or predicted performance characteristic of the first and second implants. For example, using the computational simulation methods described above, prior to an actual operation, a surgeon may simulate implanting components into a joint. Generally, a surgeon will simulate placing the components in an ideal pose. However, if the initial pose chosen by the surgeon does not suitably fit the bone, the surgeon may change the pose of the implant to provide a better anatomic fit. The computing device running the simulation is programmed to provide predicted performance data for the newly positioned implant. The data allows a surgeon to position the implant component to provide a solution specific to each patient's medical profile. For example, a surgeon may wish to optimize the fixation strength of an implant component for a very active patient. The computational simulation aides the surgeon in discovering a component implant position that will optimize the predicted fixation strength.

The ability to communicate information from the component via the feature and the detection device provides capabilities in addition to positioning. For example, when piezoelectric transducers have been embedded in the component, a piezoelectric measuring system can be used to measure piezoelectric voltage patterns generated in response to deflections of the component during or after surgery. As the component experiences wear over time, the deflection pattern of the component will change, which will cause a corresponding change in the voltage pattern generated by the piezoelectric transducers. Differences in the voltage pattern over time can be detected and used to quantify wear of the component.

As another example, the feature can provide information about the component during the life of the implant in a non-invasive manner. For example, when the feature includes a passive RFID tag, a surgeon can interrogate the RFID tag through the skin and muscle of the patient using an RFID reader. In this manner, the surgeon can determine a position and an orientation of the component in the joint without opening the joint to expose the implant. By capturing data with the joint in various positions (loaded and unloaded), the computing device can obtain relative positions of the implant components and use this data to determine, for example, relative wear between the components and the condition of soft tissue (e.g., ligaments) in the joint. As a result, implant performance and life can be monitored and the need to replace an implant component can be accurately predicted in a non-invasive manner.

According to one embodiment, a surgical method may include the steps of obtaining the positional information (pose) of previously implanted modular components, using the positional information to simulate the modular implants and determine a performance characteristic and predicted performance characteristic of the modular implants and modify the modular implants to optimize the predicted performance of the modular implant. In the alternative, one or more components of the modular implant may be replaced to optimize the predicted performance of the modular implant and joint.

Thus, according to embodiments of the present invention, an orthopedic joint prosthesis and techniques that enable improved insertion accuracy and relative placement of implant components and non-invasive monitoring of implant wear and relative position are provided.

Other embodiments of the invention will be apparent to those skilled in the art from consideration of the specification and practice of the invention disclosed herein. It is intended that the specification and examples be considered as exemplary only.

What is claimed is:

1. A system for implanting a prosthetic device comprising:
   a first component configured to be disposed in an actual joint and including a first feature; and
   a computer programmed:
      to determine, based in part on a second component that is disposed on an actual bone of the actual joint, a placement of the first component on the same actual bone to obtain a desired relationship between the first component and the second component, and
      to determine a relationship between the first component and second component,
   wherein the second component includes a second feature, and wherein the determined relationship is based at least in part on the first feature and the second feature, and wherein at least one of the first feature and the second feature includes a characteristic that is represented via a computer as a virtual feature, and
   wherein the computer is programmed to determine a rate of wear of at least one of the first component and the second component based at least in part on at least one of the first feature and the second feature.

2. A system for implanting a prosthetic device comprising:
   a first component configured to be disposed in an actual joint and including a first feature; and
   a computer programmed:
      to determine, based in part on a second component that is disposed on an actual bone of the actual joint, a placement of the first component on the same actual bone to obtain a desired relationship between the first component and the second component, and
      to determine a relationship between the first component and second component,
   wherein the second component includes a second feature, and wherein the determined relationship is based at least in part on the first feature and the second feature, and wherein at least one of the first feature and the second feature includes a characteristic that is represented via a computer as a virtual feature, and
   wherein the computer is programmed to determine a rate of wear of at least one of the first component and the second component based at least in part on the determined relationship between the first component and the second component.

* * * * *